(12) United States Patent
Yu et al.

(10) Patent No.: US 8,906,380 B2
(45) Date of Patent: Dec. 9, 2014

(54) FUNGAL IMMUNOSTIMULATORY COMPOSITIONS

(75) Inventors: Alice Yu, La Jolla, CA (US); John Yu, La Jolla, CA (US); Kuo-I Lin, Taipei (TW); Wen-Bin Yang, Taipei (TW); Chi-Huey Wong, Rancho Santa Fe, CA (US)

(73) Assignee: Academia Sinica, Nangkang, Taipei (TW)

( * ) Notice: Subject to any disclaimer, the term of this patent is extended or adjusted under 35 U.S.C. 154(b) by 1273 days.

(21) Appl. No.: 11/549,215

(22) Filed: Oct. 13, 2006

(65) Prior Publication Data

US 2007/0231339 A1   Oct. 4, 2007

Related U.S. Application Data

(60) Provisional application No. 60/727,047, filed on Oct. 14, 2005.

(51) Int. Cl.
| | |
|---|---|
| A61K 39/00 | (2006.01) |
| A61K 39/395 | (2006.01) |
| A61K 45/00 | (2006.01) |
| A61K 47/00 | (2006.01) |
| A61K 39/38 | (2006.01) |
| A61K 51/00 | (2006.01) |
| C12N 5/00 | (2006.01) |
| C12N 5/02 | (2006.01) |
| A01N 37/18 | (2006.01) |
| A61K 38/00 | (2006.01) |
| A61P 31/10 | (2006.01) |
| A61K 38/14 | (2006.01) |
| A61K 36/074 | (2006.01) |
| A61K 39/39 | (2006.01) |
| C12N 5/0784 | (2010.01) |

(52) U.S. Cl.
CPC .............. A61K 36/074 (2013.01); A61K 39/39 (2013.01); C12N 5/0639 (2013.01); *A61K 2039/57* (2013.01); *C12N 2500/74* (2013.01)
USPC .................. 424/184.1; 424/140.1; 424/278.1; 424/1.41; 435/375; 514/3.9; 514/20.9

(58) Field of Classification Search
CPC ................ A61K 36/074; A61K 36/06; A61K 2039/5154; A61K 2039/57; A61K 39/39; C12N 2500/74; C12N 5/0639
See application file for complete search history.

(56) References Cited

U.S. PATENT DOCUMENTS

| | | | |
|---|---|---|---|
| 4,522,811 | A | 6/1985 | Eppstein et al. |
| 5,334,704 | A | 8/1994 | Tsunoo et al. |
| 6,395,310 | B1 | 5/2002 | Iwasaki |
| 6,464,982 | B1 | 10/2002 | Lam |
| 6,471,860 | B1 | 10/2002 | Miltenyi et al. |
| 6,613,754 | B1 | 9/2003 | Wu |
| 7,135,183 | B1 | 11/2006 | Wang et al. |
| 7,323,176 | B2 | 1/2008 | Wang et al. |
| 7,560,114 | B2 * | 7/2009 | Wang et al. .............. 424/195.15 |
| 7,687,064 | B2 * | 3/2010 | Hua et al. .................. 424/195.15 |
| 2001/0031265 | A1 * | 10/2001 | Liu et al. ................... 424/195.15 |
| 2002/0006444 | A1 * | 1/2002 | Konishi ......................... 424/725 |
| 2003/0021857 | A1 * | 1/2003 | Tanaka et al. .................. 424/725 |
| 2003/0068329 | A1 | 4/2003 | Kosuna |
| 2003/0095981 | A1 | 5/2003 | Wong et al. |
| 2007/0104729 | A1 | 5/2007 | Wang et al. |
| 2007/0105814 | A1 * | 5/2007 | Hua et al. .......................... 514/54 |
| 2007/0231339 | A1 | 10/2007 | Yu et al. |
| 2008/0214442 | A1 | 9/2008 | Yu et al. |
| 2008/0247989 | A1 | 10/2008 | Shih et al. |

FOREIGN PATENT DOCUMENTS

| | | | |
|---|---|---|---|
| JP | 60-078567 | * | 4/1985 |
| WO | WO2006/044616 | | 4/2006 |

OTHER PUBLICATIONS

Gao et al. (International Journal of Medicinal Mushrooms, 2002; 4: 207-214).*
Gao et al. (International Journal of Medicinal Mushrooms, 2002; 4: 321-327).*
Yeo et al. (Journal of Medicinal Virology, 2003; 70: 553-561).*
Lee et al. (International Journal of Epidemiology, 1998; 27: 316-319).*
Blomberg K. et al., *Fluorescent europium chelates as target cell markers in the assessment of natural killer cell cytotoxicity*, J. Immunol. Methods, 1993, vol. 160, pp. 27-34.
Bowden, R. et al., *Alteration of Cytokine Levels in Murine Retrovirus Infection: Modulation by Combination Therapy*, International Journal of Immunopharmacology 1999, vol. 21, pp. 815-827.
Braciale T. et al., *Antigen presentation: structural themes and functional variations*, Immunology Today, 1991, vol. 12, No. 4, pp. 124-129.
Bronte V. et al., *IL-2 Enhances the Function of Recombinant Poxvirus-Based Vaccines in the Treatment of Established Pulmonary Metastases*, J. Immunol., 1995, vol. 154, pp. 5282-5292.
Chen H. et al., *Studies on the immuno-modulating and anti-tumor activities of Ganoderma lucidum (Reishi) polysaccharides*, Bioorg. Med. Chem., 2004, vol. 12, pp. 5595-5601.
Chen-Bettecken U. et al., *IgM RNA switch from membrane to secretory form is prevented by adding antireceptor antibody to bacterial lipopolysaccharide-stimulated murine primary B-cell cultures*, Proc. Natl. Acad. Sci., USA, 1985, vol. 82, pp. 7384-7388.

(Continued)

*Primary Examiner* — Gary Nickol
*Assistant Examiner* — Lakia Tongue
(74) *Attorney, Agent, or Firm* — Eckman Basu LLP

(57) ABSTRACT

Methods are disclosed which are useful in increasing maturation of dendritic cells from CD14+ mononuclear cells, by contact with a composition comprising a fucose-containing glycoprotein fraction from *Ganoderma lucidum*. The extract can also be used for increasing production of a cytokine or a chemokine in a dendritic cell or CD19+ B cell. In addition, a fucose-containing glycoprotein fraction from *Ganoderma lucidum* can be administered to a subject identified as needing increased immunoglobulin, cytokine, or chemokine production.

7 Claims, 7 Drawing Sheets

(56) References Cited

OTHER PUBLICATIONS

Chien C., *Polysaccharides of Ganoderma lucidum alter cell immunophenotypic expression and enhance CD56+NK-cell cytotoxicity in cord blood*, Bioorg. Med. Chem., 2004, vol. 12, pp. 5603-5609.

U.S. Appl. No. 60/727,047, filed Oct. 14, 2005, Yu et al.

Feltkamp M. et al., *Cytotoxic T lymphocytes raised against a subdominant epitope offered as a synthetic peptide eradicate human papillomavirus type 16-induced tumors*, Eur. J. Immunol., 1995, vol. 25, pp. 2638-2642.

Franz, G., *Polysaccharides in Pharmacy: Current Applications and Future Concepts*, Planta Medica, 1989, vol. 55, pp. 493-497.

Furusawa, E. et al., *Antitumor Activity of Ganoderma lucidum, an Edible Mushroom, on Intraperitoneally Implanted Lewis Lung Carcinoma in Synergenic Mice*, Phytotherapy Research, vol. 6, 1992, pp. 300-304.

Grohmann U. et al, *CD8+cell activation to a major mastocytoma rejection antigen, P815AB: requirement for tumor helper peptides in priming for skin test reactivity to a P815AB-related peptide*, Eur. J. Immunol., 1995, vol. 25, pp. 2797-2802.

Halhoul M. et al., *Differential Determination of Glucose and Fructose, and Glucose- and Fructose-Yielding Substances with Anthrone*, Anal. Biochem., 1972, vol. 50, pp. 337-343.

Hellman M. et al., *Separation of Isomeric Polyphenyls by Adsorption Chromatography*, 1990, Analytical Chemistry, pp. 1206-1210.

Henderson R. et al., *Human Tumor Antigens are Ready to Fly*, Advances in Immunology, 1996, vol. 62, pp. 217-256.

Hsu H. et al., *Extract of Reishi Polysaccharides Induces Cytokine Expression via TLR4-Modulated Protein Kinase Signaling Pathways*, J. Immunol., 2004, vol. 173, pp. 5989-5999.

Jermyn M., *Increasing the Sensitivity of the Anthrone Method for Carbohydrate*, Anal. Biochem., 1975, vol. 68, pp. 332-335.

Kim B. et al., *Antineoplastic Components of Korean Basidomycetes*, Korean Journal of Mycology, 1980, vol. 8, No. 2, pp. 107-114.

Kovacsovics-Bankowski M. et al., *A Phagosome-to-Cytosol Pathway for Exogenous Antigens Presented on MHC Class I Molecules*, Science, 1995, vol. 267, pp. 243-246.

Lin K. et al., *Reishi Polysaccharides Induce Immunoglobulin Production through the TLR4/TLR2-mediated Induction of Transcription Factor Blimp-I*, J. Biol. Chem., 2006, vol. 281, No. 34, pp. 24111-24123.

Lo C. et al., *Simple fractionation of phospholipase $A_2$ analogues from snake venom by high-performance liquid chromatography*, J. Chromatogr. 1990, vol. 530, pp. 129-136.

Miyazaki, T. et al., *Structural Examination of an Alkali-Extracted, Water-Soluble Heteroglycan of the Fungus Ganoderma lucidum*, Carbohydrate Research, 1982, vol. 109, pp. 290-294.

Mizuno et al., *Fractionation, Chemical Modification and Antitumor Activity of Water-insoluble Polysaccharides of the Fruiting Body of Ganoderma lucidum*, Journal of the Agricultural Chemical Society of Japan (Nippon Nôgeikagaku Kaishi), 1985, vol. 59, No. 11, pp. 1143-1151. [English language abstract enclosed].

Mosmann, T., *Rapid Colorimetric Assay for Cellular Growth and Survival: Application to Proliferation and Cytotoxicity Assays*, Journal of Immunological Methods, 1983, vol. 65, pp. 55-63.

Müller A. et al., *Receptor Binding and Internalization of a Water-Soluble (1→3)-β-D-Glucan Biologic Response Modifier in Two Monocyte/Macrophage Cell Lines*, J. Immunol., 1996, vol. 156, pp. 3418-3425.

Murphy, E. et al., *Detection of in vivo expression of interleukin-10 using a semi-quantitative polymerase chain reaction method in Schistosoma mansoni Infected Mice*, Journal of Immunological Methods, 1993, vol. 162, pp. 211-223.

Norkin L. et al., *Association of Caveolin with Chlamydia trachomatis Inclusions at Early and Late Stages of Infection*, Exp. Cell. Res., 2001, vol. 266, pp. 229-238.

Puccetti P. et al., *Use of a skin test assay to determine tumor-specific CD8+ T cell reactivity*, Eur. J. Immuno., 1994, vol. 24, pp. 1446-1452.

Robbins P. et al., *A Mutated β-Catenin Gene Encodes a Melanoma-specific Antigen Recognized by Tumor Infiltrating Lymphocytes*, J. Exp. Med., 1996, vol. 183, pp. 1185-1192.

Sanchez, J. et al., *The mouse Swiss-2D Page database: a tool for proteomics study of diabetes and obesity*, Proteomics, 2001, vol. 1, pp. 136-163.

Shaffer A.,*XBP 1, Downstream of Blimp-I, Expands the Secretory Apparatus and Other Organelles, and Increases Protein Synthesis in Plasma Cell Differentiation*, Immunity, 2004, vol. 21, pp. 81-93.

Shao B. et al., *Immune receptors for polysaccharides from Ganoderma lucidum*, Biochem. Biophys. Res. Commun., 2004, vol. 323, pp. 133-141.

Shapiro-Shelef M. et al., *Blimp-I is Required for the Formation of Immunoglobulin Secreting Plasma Cells and Pre-Plasma Memory B Cells*, Immunity, 2003, vol. 19, pp. 607-620.

Shiao M. et al., *Natural Products and Biological Activities of the Chinese Medicinal Fungus Ganoderma lucidum*, American Chemical Society, 1994, pp. 342-354.

Sieckmann D. et al., *Activation of Mouse Lymphocytes by Anti-Immunoglobulin*, J. Exp. Med., 1978, vol. 147, pp. 814-829.

Smith J. et al., *Current Protocols in Molecular Biology*, John Wiley & Sons, Inc., 2005, Sec. 11.1-11.3.

Somani B. et al., *A Modified Anthrone-Sulfuric Acid Method for the Determination of Fructose in the Presence of Certain Proteins*, Anal. Biochem., 1987, vol. 167, p. 327-330.

Sone Y. et al. *Structures and Antitumor Activities of the Polysaccharides Isolated from Fruiting Body and the Growing Culture of Mycelium of Ganoderma lucidum*, Agric. Biol. Chem., 1985, vol. 49, pp. 2641-2653.

Spackman D. et al., *Automatic Recording Apparatus for Use in the Chromatography of Amino Acids*, Anal. Chem., 1958, vol. 30, pp. 1190-1206.

Usui, T. et al. *Isolation and characterization of antitumor active β-D-glucans from the fruit bodies of Ganoderma applanatum*, Carbohydrate Research, 1983, vol. 115, pp. 273-280.

Van Strijp J. et al., *Ligand Specificity of Purified Complement Receptor Type Three ($CD11b/CD18, \alpha_m\beta_2$, Mac-1)*, J. Immunol., 1993, vol. 151, pp. 3324-3336.

Větvička V. et al., *Soluble β-Glucan Polysaccharide Binding to the Lectin Site of Neutrophil or Natural Killer Cell Complement Receptor Type 3 (CD11b/CD18) Generates a Primed State of the Receptor Capable of Mediating Cytotoxicity of iC3b-Opsonized Target Cells*, J. Clin. Invest., 1996, vol. 98, pp. 50-61.

Vitiello A. et al., *Development of a Lipopeptide-based Therapeutic Vaccine to Treat Chronic HBV Infection*, J. Clin. Inv. 1995, vol. 95, pp. 341-349.

Wang S. et al., *The Anti-Tumor Effect of Ganoderma lucidum is Mediated by Cytokines Released from Activated Macrophages and T. Lymphocytes*, Int. J. Cancer, 1997, vol. 70, pp. 699-705.

Wang Y. et al., *Studies on the Immuno-Modulating and Antitumor Activities of Ganoderma lucidum (Reishi) Polysaccharides: Functional and Proteomic Analyses of a Fucose-Containing Glycoprotein Fraction Responsible for the Activities*, Bioorg. Med. Chem., 2002, vol. 10, pp. 1057-1062.

Widmann C. et al., *T helper epitopes enhance the cytotoxic response of mice immunized with MHC class I—restricted malaria peptides*, J. Immunol. Methods, 1992, vol. 155, pp. 95-99.

York I. et al., *Antigen Processing and Presentation by the Class I Major Histocompatibility Complex*, Annu. Rev. Immunol., 1996, vol. 14, pp. 369-396.

Zhang J. et al., *Activation of B lymphocytes by GLIS, a bioactive proteoglycan from Ganoderma lucidum*, Life Sci., 2002, vol. 71, pp. 623-638.

International Search Report, PCT/US06/37028, dated Mar. 22, 2007.

Asadullah, K. et al., *Interleukin-10 and Psoriasis*, Interleukin-10, 2006, pp. 161-168.

Raj, D. et al., *Keratinocyte Apoptosis in Epidermal Development and Disease*, J. Investigative Dermatology, 2006, vol. 126, pp. 243-257.

\* cited by examiner

Table 1.

| Cytokine | Fold increase over control | |
| --- | --- | --- |
| | Reishi Batch 1 | Reishi Batch 2 |
| TNF-alpha | 286.05 | >242.12 |
| IL-10 | >208.47 | >37.39 |
| IL-1 alpha | 53.85 | 59.47 |
| RANTES | >27.80 | >27.80 |
| IL-6 | >27.11 | 66.06 |
| IL-1 beta | >26.67 | >8.9 |
| IL-12 p70 | >25.01 | X |
| MIP-1 alpha | >17.23 | >17.23 |
| IL-12 p40 | 12.24 | 5.63 |
| IP-10 | >7.29 | >7.29 |
| Eotaxin | 4.64 | 3.81 |
| IL-3 | 3.62 | 3.54 |
| MCP-1 | 1.57 | 2.37 |
| IL-7 | 1.35 | 1.14 |
| IL-8 | 1.29 | 2.99 |
| IFN-gamma | 2.12 | 1.17 |

FIGURE 4

FUNGAL IMMUNOSTIMULATORY COMPOSITIONS

RELATED APPLICATIONS

This application claims the benefit of U.S. Provisional Application Ser. No. 60/727,047, filed Oct. 14, 2005, the entire contents of which are specifically incorporated herein by reference.

FIELD OF THE DISCLOSURE

The present disclosure refers to the field of immunology and cellular biology.

BACKGROUND OF THE DISCLOSURE

The immune system is composed of many interdependent cell types that collectively protect the body from bacterial, parasitic, fungal, viral infections and from the growth of tumor cells. Many of these cell types have specialized functions.

For example, dendritic cells play a pivotal role in inducing a primary immune response by capturing and presenting antigens to the cells of the adaptive immune system (e.g., B cells) that are responsible for the production of antibodies. In addition, both of these cell types secrete important classes of small molecular weight immunostimulatory proteins such as cytokines and chemokines.

Dendritic cell and B cell activity is compromised or insufficient in a wide range of human diseases. Thus, there is an ongoing need for compositions that increase the populations of these cells or enhance their activity in immunity.

*Ganoderma* species (a group of medicinal fungus) is known in the art. *Ganoderma lucidum* (Reishi or Ling-Zhi) has been used as traditional Chinese medicine (TCM) for promoting good health, perpetual youth, and longevity (Shiao, M. S., K. R. Lee, L. J. Lin, and C. T. Wang. in *Food Phytochemicals for Cancer Prevention II: Teas, Spices, and Herbs*. C. T. Ho, T. Osawa, M. T. Huang, and R. T. Rosen, eds. American Chemical Society, Washington D.C., 1994, p. 342-354). Extracts of Reishi have been used as anti-tumor and immuno-modulating agents. (Sone, Y., R. Okuda, N. Wada, E. Kishida, and A. Misaki, in Agric. Biol. Chem. 1985 49:2641-2653; Wang S.-Y., Hsu M.-L. and Hsu H., *Int. J. Cancer* 1997 70, pp. 699-705; Vetvicka V., Thornton B. P. and Ross G. D., *J. Clin. Invest.* 1996 98, pp. 50-61; Van Strijp J. A. G., Russel D. G., Tuomanen E., Brown E. J. and Wright S. D., *J. Immunol.* 1993 151, pp. 3324-3336; Muller A., Rice P. J., Ensley H. E., Coogan P. S., Kalbfleisch J. H., Kelley J. L., Love E. J., Portera C. A., Ha T., Browder I. W. and Williams D. L., *J. Immunol.* 1996 156, pp. 3418-3425; Lee, S. S., Y. H. Wei, C. F. Chen, S. Y. Wang, and K. Y. Chen. *Int. J. Chin. Med.* 1995 6:1-12.) A fucose-containing glycoprotein fraction of *Ganoderma lucidum* Reishi extract has been found to be useful for stimulating the expression of an inflammatory cytokine or modulating differentiation of a mononuclear cell by Wong et al., WO 2006/44616, published Apr. 27, 2006, the disclosure of which is incorporated herein by reference in its entirety.

SUMMARY OF THE DISCLOSURE

In one aspect, the disclosure provides a method for increasing maturation of dendritic cells by contacting a CD14$^+$ mononuclear cell with a composition comprising a fucose-containing glycoprotein fraction from *Ganoderma lucidum*.

In another aspect, the disclosure provides a method for increasing immunoglobulin production (e.g., IgG or IgM) in a subject by administering an effective amount of a composition comprising a fucose-containing glycoprotein fraction from *Ganoderma lucidum*.

In another aspect, the disclosure provides a method for increasing an immune response to an antigen in a subject. The method includes contacting CD14$^+$ mononuclear cells with the antigen and with a composition comprising a fucose-containing glycoprotein fraction from *Ganoderma lucidum*. The contacting can be performed ex vivo (e.g., using a cell population enriched for CD14$^+$ cells) or in vivo (e.g., by administering the antigen and the composition to the subject comprising CD14+ mononuclear cells, by the same or separate routes). In addition, CD14$^+$ mononuclear cells contacted with the antigen and the composition ex vivo can subsequently be transferred into the subject. In one embodiment, the antigen is derived from a pathogen. For example, suitable pathogens include, but are not limited to, a pathogen that causes diphtheria, tetanus, pertussis, polio, *Haemophilus Influenzae* type b, hepatitis, pneumonia, meningitis, otitis media, influenza, avian flu, chicken pox, rubeola, or rubella. The antigen can also be one that is expressed in a cancer cell.

In a further aspect, the disclosure provides a method for increasing production of a cytokine or a chemokine in a subject. The method involves administering to the subject a composition comprising a fucose-containing glycoprotein fraction from *Ganoderma lucidum*. For example, without limitation, the cytokine or chemokine can be IL-1α, IL-1β, IL-3, IL-6, IL-7, IL-8, IL-10, IL-12p40, IL-12p70, IFN-K, TNF-α, Eotaxin, IP-10, MCP-1, MIP-1α, or RANTES.

In another aspect, the disclosure provides a method of increasing production of a cytokine or chemokine in a dendritic cell by contacting the dendritic cell with a composition comprising a fucose-containing glycoprotein fraction from *Ganoderma lucidum*. For example, the cytokine or chemokine can be IL-1α, IL-1β, IL-3, IL-6, IL-7, IL-8, IL-10, IL-12p40, IL-12p70, IFN-K, TNF-α, Eotaxin, IP-10, MCP-1, MIP-1α, or RANTES. The dendritic cell can be contacted in vivo or ex vivo with the fucose-containing glycoprotein fraction.

In another aspect, the disclosure provides a method of increasing production of a cytokine or chemokine in a human CD19$^+$ cell by contacting the cell with a composition comprising a fucose-containing glycoprotein fraction from *Ganoderma lucidum*. For example, without limitation, the cytokine can be IL-6, IL-8, and MIP-1α. The CD19+ cell can be contacted in vivo or ex vivo with the fucose-containing glycoprotein fraction.

In some implementations of the methods of the disclosure, a population of cells is contacted with a composition comprising a fucose-containing glycoprotein fraction from *Ganoderma lucidum* ex vivo, and the cells are then transferred into a subject identified as in need thereof. In additional implementations of the methods of the disclosure, a population of cells in a subject, particularly a human subject, is contacted in vivo with the composition comprising a fucose-containing glycoprotein fraction from *Ganoderma lucidum* by administering the composition to the subject.

The methods of the disclosure may be used prophylactically or therapeutically.

In another aspect, the disclosure provides a method for the treatment of immunodeficiency diseases in a patient by administering a composition comprising a fucose-containing glycoprotein fraction from *Ganoderma lucidum* to the patient. Immunodeficiency diseases which may be treated by the methods of the disclosure include, but are not limited to, common variable immunodeficiency (CVID).

In another aspect, the disclosure provides a method of augmenting the immune response to a vaccine in a subject, the method comprising administering a composition comprising a fucose-containing glycoprotein fraction from *Ganoderma lucidum* to the subject either before, during, or after administration of the vaccine. In one implementation, the vaccine is designed to prevent infectious diseases, including, but not limited to, DPT, polio, HIB, hepatitis, flu vaccine, HIB, pneumococcus and influenza vaccines. In another implementation, the vaccine is a therapeutic vaccine for cancer therapy. In such implementations, the fucose-containing glycoprotein fraction serves as an adjuvant.

In a further aspect, the disclosure provides a method of augmenting the ability of an antigen presenting cell (APC) to present tumor antigens to the immune system, the method comprising: contacting the antigen presenting cell with a composition comprising a fucose-containing glycoprotein fraction from *Ganoderma lucidum*; and contacting the antigen presenting cell with at least one tumor antigen.

In another aspect, the disclosure provides an immunostimulatory composition which comprises a fucose-containing glycoprotein fraction from *Ganoderma lucidum* and at least one antigen. Suitable antigens include, but are not limited to, antigens derived from any of the following: tetanus toxoid, hemagglutinin molecules from influenza virus, cancer antigen, diphtheria toxoid, HIV gp120, IgA protease, insulin peptide B, *Spongospora subterranea* antigen, *vibriose* antigens, *Salmonella* antigens, *pneumococcus* antigens, respiratory syncytial virus antigens, *Haemophilus influenza* outer membrane proteins, *Helicobacter pylori* urease, *Neisseria meningitidis* pilins and *N. gonorrhoeae* pilins. The immunostimulatory composition may further comprise one or more excipients or carriers, including, but not limited, to: surfactants, absorption promoters, water absorbing polymers, substances which inhibit enzymatic degradation, alcohols, organic solvents, oils, pH-controlling agents, solubilizers, stabilizers, HLB-controlling agents, viscosity controlling agents, preservatives, osmotic pressure controlling agents, propellants, air displacement, water, and mixtures thereof.

Other features or advantages of the present invention will be apparent from the following detailed description, and also from the claims.

BRIEF DESCRIPTION OF THE DRAWINGS

The above-mentioned features and objects of the present disclosure will become more apparent with reference to the following description taken in conjunction with the accompanying drawings.

FIG. 4 shows a table (Table 1) of cytokine secreting profile of dendritic cells after treatment with a fucose-containing glycoprotein fraction from *Ganoderma lucidum* via commercially available Beadlyte cytokines kit. DC culture media in both treated and control group were collected. Using commercially available Beadlyte cytokines kit, 16 of 22 cytokines were significantly induced by a fucose-containing glycoprotein fraction from *Ganoderma lucidum*. Changes in each cytokine level are presented in terms of fold increase of the measurement of treated group against that of control group.

DETAILED DESCRIPTION OF THE EMBODIMENTS

Figure 1:
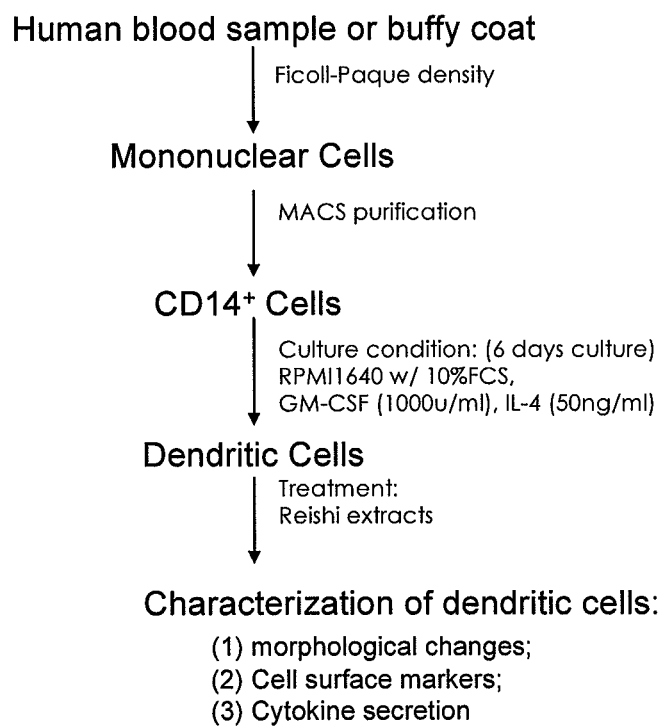
FIG. 1 shows a scheme for preparation and induction of dendritic cells

The phrase "fucose-containing glycoprotein fraction" refers to a constituent part of an extract from *Ganoderma lucidum* that includes at least one of a polysaccharide and a glycopeptide comprising fucose residues.

The fucose-containing glycoprotein fraction from *Ganoderma lucidum* is herein also referred to as "*Ganoderma lucidum* extract" or, alternatively as one of "Reishi extract", "Reishi extract F3", water-soluble extract of *Ganoderma lucidum*, "Reishi fraction F3", "Reishi-F3", "F3," "EORP," or "the extract".

The term "glycoprotein" or "glycopeptide" refers to a protein of any length and dimension with covalently attached sugar units, either bonded via the OH group of serine or threonine O glycosylated) or through the amide NH$_2$ of asparagine (N-glycosylated) or portions thereof. The term "polysaccharide" refers to a polymers of any length and dimensions comprising monosaccharide residues linked glycosidically in branched or unbranched chains.

The term "extract" refers to a concentrated preparation obtained by removing active constituents from a given substance; when the active constituents are included in a solvent, the removal of the active constituents can be performed by evaporating all or nearly all the solvent and adjusting the residual mass or powder to a prescribed standard; extracts are usually prepared in three forms, semiliquid or of syrupy consistency, pilular or solid and as dry powder.

The phrase "*Ganoderma Lucidum*" refers to fungus *Ganoderma Lucidum* or Reishi, any tissue, part or fraction therefrom and/or any preparation thereof including homogenates, suspensions, filtrates, filtration residues and solutions.

The term "preparation" refers to a composition processed, manufactured, or compounded starting from a given substance, the term "concentrated preparation" refers to a preparation with an increased ratio of the mass or volume of active constituents to the mass or volume of the non-active constituents or to the mass volume of the entire composition, compared with the same ratio in the given substance.

The term "fraction" refers to one of the separable constituents of a substance.

In some embodiments, the fucose-containing glycoprotein fraction is included in a fraction of *Ganoderma Lucidum* (herein also denominated F3, Fraction 3, extract of Reishi polysaccharide (EORP), GL(PS)_Wu, or Wu) showing a light absorbance of about 1.8 O.D. at 625 nm identified and isolated from a water-soluble extract of *Ganoderma Lucidum* (crude Reishi extract) by experimental procedures exemplified in Example 1, 2 and 3.

Fraction 3 includes a fucose-containing glycoprotein fraction, which comprises terminal fucose residues. The phrase "terminal fucose residues" identifies fucose residues of a chain of sugars located in a region proximate to a free end of a chain of sugars. The fucose-containing glycoprotein fraction of Fraction 3, also includes fucose residues bound with α-1,2-fucosidic linkages and α-3,4-fucosidic linkages.

In addition to fucose residue, fucose-containing glycoprotein fraction of Fraction 3 can also comprise glucose mannose, N-acetylglucosamine, xylose and rhamnose, as established by experimental procedures exemplified in Example 1 and Example 2.

The fucose-containing glycoprotein fraction of Fraction 3 can also include an amino acidic component, as established by experimental procedures exemplified in Example 1. The amino acidic component of Fraction 3, however, can be significantly modified without impairing the activities associated with the fucose-containing glycoprotein fraction of Fraction 3.

Reishi fraction F3 can be obtained by a process comprising: homogenizing a plant tissue of *Ganoderma Lucidum* and/or providing an homogenized plant tissue from *Ganoderma Lucidum*; extracting the homogenized plant tissue of *Ganoderma Lucidum*; and filtering the extracted homogenized plant tissue to form one or more fractions, the fractions comprising a saccharide component having fucose residues. The fractions formed in the above procedures can also be treated with protease.

The term "extracting" refers to any suitable procedure or protocol to provide an extract starting from a given substance; determination of such protocols can be accomplished by those skilled in the art depending upon a variety of variables, including the substance and the active constituents to be removed from the substance; exemplary procedures include treatment based on different solubility of the constituents of the substance in different solvents. Extracting the homogenized plant tissue can be performed by any suitable procedure or protocol to provide an extract of *Ganoderma Lucidum* including a fucose-containing glycoprotein or fucose-containing polysaccharide constituents from the homogenized plant tissue; for example a suitable procedure includes treating the homogenized plant tissue with aqueous alkalyne solution, for example 0.1 N NaOH, for a predetermined time to form a crude extract.

The term "filtering" or "filtration" refers to any suitable procedure to separate a constituent of a substance, such as an active constituent, from other constituents of the substance, such as impurities; determination of such protocols can be accomplished by those skilled in the art depending upon a variety of variables, including the substance, the active constituents and the inactive constituents of the substance; exemplary filtration procedures include dialysis and gel filtration chromatography. Filtering the extracted homogenized plant tissue can be performed by subjecting the crude extract to filtration, such as gel filtration chromatography e.g. using a Sephacryl S-500 column, and eluting with an aqueous solution to form one or more fractions. In one embodiment the aqueous solution is buffered at about pH 7.0, for example a Tris buffer solution.

In additional embodiments the fucose-containing glycoprotein fraction is included in fractions of fraction F3 (herein also collectively named subfractions), herein identified as F3G1, F3G2, F3G3, and the F3G2 sub-fractions F3G2H1 and F3G2H2. The subfractions are isolated from Fraction 3 by experimental procedures exemplified in Example 2. Hence, the term "fucose-containing glycoprotein" refers not only to fraction F3, but also to any subfractions thereof, and any combination of F3 with the subfractions, or any combination of the subfractions.

The different subfractions can be identified by the respective ability to absorb light. F3G1 shows a light absorbance of about 0.4 O.D. at 480 nm, F3G2 shows a light absorbance of about 0.1 O.D. at 480 nm; F3G2H1 shows a light absorbance of about 0.10 O.D. at 480 nm and F3G2H2 shows a light absorbance of about 0.5 O.D. at 480 nm, as established by experimental procedures exemplified in Example 2.

F3 and the subfractions are also herein collectively named fractions.

The fucose-containing glycoprotein fraction comprised in the subfractions can also include in addition to the fucose residues other sugars such as glucose and mannose galactose, N-acetylglucosamine, and xylose as established by experimental procedures exemplified in Example 2 (see in particular Table IV).

The subfractions F3G1, FG2 and F3G3 can be obtained by partitioning fraction 3. The term "partitioning" refers to any suitable procedure or protocol to divide a substance in two or more constituents thereof, determination of such protocols can be accomplished by those skilled in the art depending upon a variety of variables, including the substance, and the constituents to be partitioned. Partitioning fraction 3 can be performed by filtering fraction 3, (for example with an anion exchanger such as Diaion-WA30 anion exchanger or by gel filtration chromatography, e.g. on a TSK HW-75 column), and isolating the subfractions F3G1, F3G2 and F3G3 from the filtered fraction 3, (for example by elution with an alkaline solution, including for example at least one of NaCl).

F3G2 subfractions F3G2H1 and F3G2H2 can be obtained by subjecting F3G2 to further partitioning. For example, partitioning of F3G2 can be performed by filtering subfraction F3G2 e.g. by gel filtration chromatography e.g. on a TSK HW-75 column, and isolating the subfractions F3G2H1 and F3G2H2 from the filtered subfraction F3G2 e.g. by eluting the the filtered subfraction F3G2 with an aqueous solution.

Exemplary embodiments of the above-mentioned process to obtain the subfractions are illustrated in Example 2.

The term "effective amount" of a compound is at least the minimum amount of the compound that is necessary to minimally achieve, and more preferably, optimally achieve, the desired effect. The term "an effective amount" refers to the amount of a fucose-containing glycoprotein fraction from *Ganoderma lucidum* that is required to confer a specific prophylactic or therapeutic effect on the treated subject (e.g., increased cytokine production, increased immunoglobulin production, or an increased immune response to an antigen). An effective amount of fucose-containing glycoprotein fraction for use in a given method can be readily determined by one skilled in the art without undue experimentation, depending upon the particular circumstances encountered (e.g. concentrations, cell type and number, etc.) upon reading of the present disclosure and in particular the Examples section.

Effective doses will vary, as recognized by those skilled in the art, depending on the specific immunological effect to be evoked (e.g., increased immunoglobulin M production), the severity of the immunological condition, the general health or age of the subject, previous treatments, route of administration, excipient usage, and the possibility of co-usage with other prophylactic or therapeutic treatment.

An active composition containing an effective amount of a fucose-containing glycoprotein fraction from *Ganoderma lucidum* can be administered parenterally, orally, nasally, rectally, topically, or buccally. The term "parenteral" as used herein refers to subcutaneous, intracutaneous, intravenous, intramuscular, intra-articular, intra-arterial, intrasynovial, intrasternal, intrathecal, or intralesional, as well as any suitable infusion technique.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery. Examples of other carriers include colloidal silicon oxide, magnesium stearate, cellulose, sodium lauryl sulfate, and D&C Yellow #10.

The term "administering" refers to any process or protocol suitable to put a compound, and in particular the fucose-containing glycoprotein fraction, in contact with the cell, wherein the term "contact" or the phrase "put in contact" mean to place the compound and in particular the fucose-containing glycoprotein fraction and the cell, in a mutual spatial relationship such that a biological interaction between the compound and the cell is feasible; the phrase "biological interaction" refers to the process by which a compound and in particular the fucose-containing glycoprotein fraction controls, influences or otherwise affects the normal functioning and/or survival of the cell; determination of such protocols can be accomplished by those skilled in the art depending upon a variety of variables, including the type of cell, whether the contact occurs in vitro, in vivo or ex vivo. Acceptable protocols to administer the fucose-containing glycoprotein fraction from *Ganoderma lucidum* include individual dose size, number of doses, frequency of dose administration, and mode of administration, such as topical administration, local administration, or oral administration in vivo, incubation and assays in vitro, or ex vivo administration e.g. to isolated dendritic cells, which can be identified by a person skilled in the art upon reading of the present disclosure and, in particular, the Examples section.

"Antigens" are any molecules which are recognized by the immune system and induce an immune reaction. The term "antigen" is intended to include a molecule which contains one or more epitopes which stimulate a host's immune system to produce a humoral, cellular and/or secretory immunological response. The antigen of the invention can be a subunit antigen, as well as killed, attenuated or inactivated bacteria, viruses, protozoa, fungi, parasites or other microbes. The antigen can be, for example, a protein, peptide, polysaccharide, lipid or DNA antigen. Suitable antigens can be derived from, for example, *Pasteurella, Actinobacillus, Chlamydia, Moraxella, Neisseria, Streptococcus, Haemophilus, Salmonella* and *Eimeria* species, as well as rotaviruses, herpes viruses (e.g., BHV-1, EHV-1), PRV, parvovirus, rabiesvirus, influenza viruses, parainfluenza viruses, hepatitis viruses, HIV, picornaviruses, tumor antigens, hormones, hormone analogs and the like.

As used herein, an "immune response" or "immunological response" to a particular antigen is intended to include the production of a secretory, cellular, humoral or antibody-mediated response to the antigen (or a generalized response). The manifestation of the response in the immunized host can include the production of antibodies (e.g., IgA, IgD, IgE, IgG or IgM antibodies), proliferation of B and/or T lymphocytes, stimulation of cytotoxic T lymphocytes that recognize antigen-presenting cells, expansion of T cell populations and the potentiation of signals which cause differentiation, activation or growth of cells of the immune system.

Typically the administration of the adjuvants of the invention will cause or result in an enhanced immune response to an antigen of interest. In this context, "enhanced" is intended to mean that the immune response to the antigen is quantitatively greater and/or qualitatively better in the presence of the adjuvant than in the absence of the adjuvant. Comparisons of immune responses in the presence and absence of the adjuvants can be performed by routine methods, such as antibody titer comparisons by radioimmunoassay or ELISA of formulations comprising adjuvant and antigen, and appropriate controls. The enhanced immune response can be a result of a direct effect on the immune system of the individual (e.g., a priming of T and B cells to increase the response to the antigen) or can result from a more advantageous presentation of the antigen to the mucus membrane (e.g., by providing better adhesion to the mucus membrane to allow a longer period of contact between the antigen and the mucus membrane, or by enhancing the absorption of the antigen across the mucus membrane, for example by increasing the permeability of the mucus membrane).

"Adjuvants" of the invention can be used as described herein as adjuvants to enhance the immunological response to an antigen. In a particular embodiment the adjuvant is a mucosal adjuvant. For example, the adjuvant can be used in a composition to immunize a mammal against a particular pathogen or subunit antigen, or to prime an immune response to a particular antigen.

The term "cellular immune response" denotes in particular the cytotoxic T-cell immunity which, as a result of the generation of cytotoxic CD8-positive T-cells and CD4-positive helper-T-cells, brings about destruction of the tumour cells or of the cells attacked by the pathogen.

The expression "humoral immune response" denotes the production of immunoglobulins which selectively recognize antigens and consequently, together with other systems such as, for example, complement, ADCC (antibody dependent cytotoxicity) or phagocytosis, bring about the destruction of these tumour cells or the cells attacked by the pathogenic agents.

The disclosure provides a number of methods for inducing immunostimulatory alterations in the functions of specific immune system cell populations, ex vivo or in vivo, by exposing them to a fucose-containing glycoprotein fraction from *Ganoderma lucidum*. The methods are useful for treatment of a number of immunological disorders or conditions as described below.

The fucose-containing glycoprotein fraction from *Ganoderma lucidum* described herein contains a polysaccharide or glycopeptide having terminal fucose residues with α-1,2-fucosidic linkages. For details, see, e.g., Wang et al. (2002) *Biorganic & Medicinal Chemistry* 10:1057-1062. Non-limiting examples of methods that can be used to prepare the fucose-containing glycoprotein fraction are described in Examples 1-3.

The fucose-containing glycoprotein fraction from *Ganoderma lucidum* induces cell-type specific immunostimulatory effects. Thus, in some implementations of the methods of the disclosure, compositions comprising the fucose-containing glycoprotein fraction can be applied ex vivo to an isolated cell type-enriched population such as a $CD14^+$ mononuclear cell population, a dendritic cell population derived therefrom, or a $CD19^+$ mononuclear cell population. A cell type-enriched population is one in which a greater proportion of the cells in the population have similar expression of cell type-specific surface protein markers (i.e., the same "immunophenotype") than in a non-enriched population e.g. relative to the cell population which was used as the starting material for the enrichment process.

An enriched cell type-specific population from peripheral blood can be obtained according to any standard method known in the art. In one non-limiting example, a buffy coat is initially prepared from a peripheral whole blood sample from a mammal (e.g., a human or a mouse). The buffy coat can be obtained by a standard procedure such as centrifuging whole blood at low speed (e.g., 200×g), and then collecting the resulting upper layer. A heterogeneous mononuclear cell population can be obtained by centrifuging the buffy coat against a Ficoll-Paque plus (Amersham Bioscience) density gradient (e.g., at 400×g for 30-40 minutes), and then collecting the resulting interface layer.

Enriched populations of specific cell types can be isolated from the heterogeneous mononuclear cell preparation by a number of standard techniques. Enriched cell-type-specific populations are readily isolated by separating cells by immunophenotype.

For example, an enriched CD14.sup.+ mononuclear cell population or an enriched CD19.sup.+ B cell population can be obtained by incubating a heterogeneous mononuclear cell preparation with magnetic microbeads conjugated to an anti-CD14 antibody or an anti-CD19 antibody, respectively. Subsequently, the microbead-bound cells are separated from unbound cells by application of a magnetic field, a technique known as magnetic activated cell sorting (MACS), to obtain population enriched for cells expressing the marker(s) of interest. The details of the MACS technique are described in, e.g., U.S. Pat. No. 6,471,860. MACS® systems are commercially available, e.g., from Miltenyi Biotech, GmbH (Bergisch Gladbach, Germany).

Other techniques for sorting as well as analyzing the presence of specific cell populations are known, e.g., fluorescence activated cell sorting (FACS) or flow cytometry. See, e.g., Norkin et al., Exp. Cell. Res. 266(2):229-38 (2001); Handbook of Flow Cytometry Methods, J. Paul Robinson (Editor) Wiley (1993); and Guide To Flow Cytometry Methods, W. McLean, Grogan James, M. Collins., Marcel Dekker, Inc, New York, (1990).

Alternatively, compositions comprising the fucose-containing glycoprotein fraction can be administered to a subject in order to induce cell-type specific effects in vivo on the CD14+ mononuclear cells and the CD19+ mononuclear cells that are present within the subject.

In one aspect, the disclosure provides a method for increasing maturation of a dendritic cell by contacting a $CD14^+$ mononuclear cell with a composition comprising a fucose-containing glycoprotein fraction from *Ganoderma lucidum*. The extract also increases production of a number of cytokines and chemokines by both dendritic cells and $CD19^+$ B cells. In addition, the fucose-containing glycoprotein fraction also stimulates the production of IgG and IgM by $CD19^+$ B cells.

The contacting can be performed ex vivo (e.g., using a cell population enriched for $CD14^+$ cells) or in vivo (e.g., by administering the composition comprising the fucose-containing glycoprotein fraction to a subject).

A fucose-containing glycoprotein fraction from *Ganoderma lucidum* applied to $CD14^+$ mononuclear cells enhances differentiation of $CD14^+$ cells into dendritic cells, and increases maturation and survival of the resulting dendritic cells. $CD14^+$ mononuclear cells express the cell surface markers CD14 and CD86. However, as these cells differentiate into mature dendritic cells, CD14 expression decreases and CD1a, CD40, CD80, and CD83 expression increases. In other words, the differentiating and maturing cells adopt an "immunophenotype" distinct from that of $CD14^+$ mononuclear cells.

A non-limiting example illustrating an ex vivo implementation of the aforementioned method is now provided. Specifically, an enriched $CD14^+$ mononuclear cell population can be differentiated into mature dendritic cells by culturing the $CD14^+$ cells, starting from day 1, in RPMI1640 medium supplemented with 10% fetal calf serum, GM-CSF (1000 U/mL), and IL-4 (50 ng/mL). The fucose-containing glycoprotein fraction is then added to the cultured population after six days, at a concentration of 1-100 µg/mL (e.g., 10 µg) for a period of 24 hours. Alternatively, the $CD14^+$ population can be cultured initially in the presence of fucose-containing glycoprotein extract, but in the absence of GM-CSF and IL-4. The resulting population of mature dendritic cells can be transferred (e.g., by direct injection into the bloodstream) to a subject identified as needing an increased population of mature dendritic cells (e.g., an individual that has undergone immunosuppressive treatment). Preferably, though not exclusively, the population of cells to be transferred to the subject is autologous.

The maturation of dendritic cells from CD $14^+$ mononuclear cells vis-a-vis changes in immunophenotype can be assessed by a number of established techniques, e.g., FACS as described in further detail below. Regardless of the specific technique adopted, the determination or selection of an immunophenotype generally relies on specific monoclonal or polyclonal antibodies against each of the relevant cell type-specific markers, e.g., CD1a, CD14, CD19, CD40, CD83, and CD86. Antibodies to these proteins are commercially available, e.g., from ABCAM®, Inc. (Cambridge, Mass.).

FACS is particularly useful for quantitatively determining the immunophenotypes present in a cell population at different times (e.g., during the differentiation of $CD14^+$ Typically, in flow cytometry, cells labeled with fluorescently labeled antibody to a cell surface marker are passed through a slender flow cell along with a sheath fluid so that the cells flow in single file. The individual cells in the flow are irradiated one at a time with a light beam (such as a laser beam) by means of hydrodynamic focusing, and the intensity of scattered light or fluorescent light from the cells, e.g., light information indicative of the cells, is measured instantaneously to analyze the cells. Flow cytometry of this kind is advantageous in that a large number of cells can be analyzed at high speed and with great accuracy.

Flow cytometers are well known in the art and are commercially available from, e.g., Beckman Coulter and Becton, Dickinson and Company.

Skilled practitioners will appreciate that many variations and/or additions to basic flow cytometry systems can be made, e.g., providing practitioners with additional and/or different analyzing capabilities. Further, skilled practitioners will appreciate that flow cytometry can be performed in an automated manner and that a flow cytometer can be provided as part of a larger, automated system, e.g., a high-throughput system.

The differentiation of CD14$^+$ cells into mature dendritic cells, in the presence of a fucose-containing glycoprotein fraction from *Ganoderma lucidum*, is also characterized by a greater fraction of the differentiating cell population adhering tightly to a culture substrate, and adopting an elongated cell shape. Such morphological changes to cell shape are readily observed by conventional bright-field light microscopy techniques (e.g., phase contrast or differential interference contrast (DIC) microscopy).

In another aspect, the disclosure provides a method for increasing an immune response to an antigen in a subject. The method includes contacting a population of cells comprising CD14$^+$ mononuclear cells with the antigen and with a composition comprising a fucose-containing glycoprotein fraction from *Ganoderma lucidum*. The contacting can be performed ex vivo (e.g., a cell population enriched for CD14$^+$ cells) or in vivo (e.g., by administering the antigen and the composition to the subject comprising CD14$^+$ mononuclear cells, by the same or separate routes). In one implementation, the CD14$^+$ mononuclear cells are cultivated in the presence of a fucose-containing glycoprotein fraction from *Ganoderma lucidum* and the antigen for a period sufficient to allow maturation of dendritic cells, as described above. After the culture period, dendritic cells (i.e., including dendritic cells that display the antigen) are then transferred to the subject, whereby the immune response to the antigen is increased. In one implementation, the antigen is derived from a pathogen. Relevant pathogens include, but are not limited to, those that cause diphtheria, tetanus, pertussis, polio, *Haemophilus influenzae* type B, hepatitis, pneumonia, meningitis, otitis media, influenza, avian flu, chicken pox, rubeola, or rubella. The selected antigen can also be one that is present at a higher level in a cancer cell than in a non-cancerous cell of a similar cell lineage. As noted above, the fucose-containing glycoprotein fraction facilitates the differentiation of CD14$^+$ cells into dendritic cells, and enhances the maturation and survival of the dendritic cells. Without being bound by theory or hypothesis, it is thought that boosting the maturation of dendritic cells in the presence of an antigen promotes the antigen presentation function of the matured dendritic cells, and thereby enhance immunity to the presented antigen.

In another aspect, the disclosure provides a method of increasing production of a cytokine or chemokine in a human CD19$^+$ cell by contacting the cell with a composition comprising a fucose-containing glycoprotein fraction from *Ganoderma lucidum*. For example, without limitation, the cytokine can be IL-6, IL-8, or MIP-1α. The CD19$^+$ cell can be contacted in vivo or ex vivo (for example using a cell population enriched for CD19$^+$ cells) with the fucose-containing glycoprotein.

In another aspect, the disclosure provides a method of increasing production of a cytokine or chemokine in a dendritic cell by contacting the dendritic cell with a composition comprising a fucose-containing glycoprotein fraction from *Ganoderma lucidum*. For example, the cytokine or chemokine can be IL-1α, IL-1β, IL-3, IL-6, IL-7, IL-8, IL-10, IL-12p40, IL-12p70, IFN-K, TNF-α, Eotaxin, IP-10, MCP-1, MIP-1α, or RANTES. The dendritic cell can be contacted in vivo or ex vivo (for example, using a cell population enriched for dendritic cells) with the fucose-containing glycoprotein.

As disclosed above, cell populations can be contacted with a composition comprising the fucose-containing glycoprotein fraction in vivo and/or ex vivo. For example, a cell population enriched for CD19$^+$ cells can be contacted ex vivo with the fucose-containing glycoprotein fraction, and then infused into a subject identified as needing an increased production of a cytokine or chemokine from CD19$^+$ B cells, as well as subjects identified as needing an increased cytokine or chemokine level, and increased immunoglobulin production from CD19$^+$ B cells.

Various assays are well established for determining the concentration of any of the various cytokines (e.g., TNF-α, IL-10, IL-1α, IL-1β, IL-3, IL-6, IL-7, IL-8, IP-10, IL-12 p40, IL-12p70, and IFN-K) or chemokines (e.g., Eotaxin, MIP-1α, and RANTES). Essentially, the various assays utilize cytokine-specific monoclonal or polyclonal antibodies to label and quantify each cytokine of interest. For example, a BEADLYTE® multiplex assay can be used to simultaneously assay the concentrations of up to cytokines present in culture medium (MILLIPORE, Billerica, Mass.).

Compositions comprising the fucose-containing glycoprotein fraction can also be administered directly to a subject in order to contact CD19+ cells and/or dendritic cells. For example, an effective amount of a composition comprising a fucose-containing glycoprotein fraction from *Ganoderma lucidum* can be administered to a subject identified as needing an increased immune response to a selected antigen. The antigen and the effective amount of a fucose-containing glycoprotein fraction from *Ganoderma lucidum* can elicit an increased immune response in the subject via the effect of the fucose-containing glycoprotein fraction on dendritic cell maturation. The fucose-containing glycoprotein fraction from *Ganoderma lucidum* and the antigen can be administered to the subject together or at separate times and/or by separate routes. For example, the effective amount of the fucose-containing glycoprotein fraction from *Ganoderma lucidum* can be administered orally, and the antigen administered by injection.

In another aspect, the disclosure provides a method for increasing immunoglobulin production (e.g., IgG or IgM) in a subject. For example, prior to the administration of the composition, the subject may be identified as suffering from hypogammaglobulinemia, common variable immunodeficiency, immunodeficiency associated with cancer, or immunosuppression. Immunoglobulin production is increased in the subject by administering an effective amount of a composition comprising a fucose-containing glycoprotein fraction from *Ganoderma lucidum*. The concentration of an immunoglobulin (e.g., immunoglobulin M) can be determined by various immunoassays including, e.g., competitive and non-competitive assays, radioimmunoassays, bioluminescence and chemiluminescence assays, fluorometric assays, sandwich assay, dot blots, and enzyme linked assays (including ELISA). For each method, the range, sensitivity, precision, reliability, specificity and reproducibility of the assay is established. Examples of some immunoassays are described in detail in, e.g., *Current Protocols in Molecular Biology*, John Wiley & Sons, N.Y. (2005), 11.1-11.3.

In a further aspect, the disclosure provides a method for increasing production of a cytokine or a chemokine in a subject. For example, without limitation, the cytokine or chemokine can be IL-1α, IL-1β, IL-3, IL-6, IL-7, IL-8, IL-10, IL-12p40, IL-12p70, IFN-K, TNF-α, Eotaxin, IP-10, MCP-1, MIP-1α, or RANTES. The method involves administering to the subject a composition comprising a fucose-containing glycoprotein fraction from *Ganoderma lucidum*. For example, the subject may be identified as suffering from chronic myeloid leukemia, or any other immune condition that could be ameliorated by an increase in the production of the above-mentioned cytokines and chemokines.

In a further aspect of the disclosure, the fucose-containing glycoprotein fraction from *Ganoderma lucidum* is utilized as an adjuvant to enhance an immune response to an antigen or vaccine. In such methods, a composition comprising a fucose-containing glycoprotein fraction from *Ganoderma lucidum* is administered to the subject either before, during, or after administration of the vaccine or antigen in order to augment the immune response to the antigen or vaccine. In one implementation, the fucose-containing glycoprotein fraction is co-administered with the vaccine or antigen by administering a mixture of the fucose-containing glycoprotein fraction and the vaccine or antigen. In one specific non-limiting example, an adjuvant comprising 0.01-70% v/v of a fucose-containing glycoprotein fraction from *Ganoderma lucidum* is used.

Parenteral administration (intramuscular and subcutaneous) of antigens or vaccines is one effective route of administration.

In one implementation, the fucose-containing glycoprotein is used as an adjuvant for the mucosal administration of antigens and vaccines. The mucosal membrane contains numerous dendritic cells which are excellent antigen-presenting cells. The mucosal membranes are also connected to lymphoid organs, called mucosal-associated lymphoid tissue, which are able to potentiate an immune response to other mucosal areas. The extensive network of blood capillaries under the nasal mucosa and the high density of T and B cells are particularly suited to provide rapid recognition of the antigen and to provide a quick immunological response. The compositions of the present disclosure may provide enhanced adhesion of the antigen to the mucosal membrane, as well as enhanced absorption of the antigen through the mucus membrane. Use of the compositions of the disclosure provides the ability to elicit a systemic (e.g., antibodies of the IgG isotype) immune response.

The compositions of the disclosure modulate the immune response to the antigen; i.e. the immunogenic or vaccine composition is capable of quantitatively and/or qualitatively improving the vaccinated host's antibody response. The numbers of antibodies produced upon immunization with the antigen may be increased (e.g., a quantitative improvement), or the profile of the immune response may be altered; for example, from a Th1 response to a Th2 response (e.g., a qualitative improvement).

Suitable antigens for the vaccine compositions of the present invention include any molecule capable of producing antibody or cell-mediated immunological response directed specifically against that entity in a vertebrate exposed to the antigen. One or more antigens may be employed. The antigen or antigens may be derived from pathogenic microorganisms including viruses, bacteria, mycoplasmas, fungi, protozoa and other parasites. Further, the antigen or antigens may be derived from sources other than microorganism, for example, cancer cells or allergens. The antigen or antigens may be all or part of a pathogenic microorganism, or all or part of a protein, glycoprotein, glycolipid, polysaccharide or lipopolysaccharide which is associated with the organism.

Pathogenic microorganisms from which antigens may be derived or produced for vaccine purposes are well known in the field of infectious diseases, as listed in, for example, Medical Microbiology, Second Edition, (1990) J. C. Sherris (ed.), Elsevier Science Publishing Co., Inc., New York.

For immunization against pathogenic agents of disease such as bacteria, viruses and parasites, proteins or peptides are used which constitute a protein of the pathogen or pathogens in question or are derived therefrom. Particularly suitable are proteins which are unaffected by the high general mutation rate of these pathogens. Published examples include HPV16/17 (Human Papilloma Virus; Feltkamp, M. C. et al., 1995, *Eur. J. Immunol.* 25 (9), 2638-2642), Hepatitis B Virus Core Antigen (Vitiello, A. et al., 1995, *J. Clin. Inv.* 95, 1, 341-349), Plasmodium Bergheii (Widmann, C. et al., 1992, *J. Immunol. Methods* 155 (1), 95-99), influenza virus nucleoprotein and hepatitis C virus.

The immunological adjuvant activity of the fucose-containing glycoprotein fraction from *Ganoderma lucidum*, either alone or with a particular antigen, can be assessed using methods known in the art, such as ELISAs, hemagglutination assays and neutralization assays. As used herein, "immunological adjuvant activity" is intended to mean the ability to potentiate an immunological response in a host to which the adjuvant and antigen are administered. Typically the adjuvant will be administered with the antigen, either in the same admixture or composition (International Publication No. WO 93/05789), or at the same time but in a separate composition or formulation. The antigen can be bound to the adjuvant (e.g., covalently) or merely admixed therewith. The adjuvant can also be administered prior to or subsequent to the administration of the antigen. Adjuvant activity includes, but is not limited to, the ability to enhance the immunological response to the antigen by increasing the immunogenicity of the antigen or by reducing the dose or level of antigen required to produce an immune response.

In one implementation, a composition comprising a fucose-containing glycoprotein fraction from *Ganoderma lucidum* is used as an adjuvant to enhance immunogenicity in an anti-cancer therapeutic composition, or vaccine, based on tumor cells, or tumor antigens. Examples of suitable tumor antigens are given in review articles published by Robbins, P. F. and Rosenberg, S. A., 1996, Journ. Exp. Med. 183, 1185-92, and Henderson, R. A., and Finn, O. J. 1996, Advances in Immunology 62, 217-256.

In order to achieve an anti-tumor response, the tumor cells must express antigens which do not occur on normal cells, or occur only to the extent that the immune system can distinguish qualitatively between normal and tumor tissue. Secondly, the immune system must be activated accordingly in order to react to these antigens. One problem in the development of human immune therapy of tumors is low tumor cell immunogenicity.

A central role is played in the regulation of a specific immune response by a trimolecular complex consisting of the components of T-cell-antigen receptor, MHC (Major Histocompatibility Complex) molecule and the ligand thereof which is a peptide fragment derived from a protein. Human MHC molecules are also referred to as HLA (Human Leucocyte Antigen) in accordance with international conventions.

Regular, degenerate and foreign gene products, e.g. viral proteins or tumor antigens, are broken down inside the cell into small peptides; some of them constitute potential ligands for MHC molecules. This provides the prerequisite for their presentation by MHC-molecules and the subsequent triggering of a cellular immune response, although it has not yet been clearly explained how the peptides are produced as MHC ligands in the cell. Foreign antigens and the fragments thereof may also be recognized, bound and eliminated by immunoglobulins which constitute the humoral immune response. This is also true of tumor antigens: using the example of tumor associated antigens MUC1, CEA and HER2/neu it has been shown that immunoglobulins which have specificity for these proteins are able to recognize and kill the protein-carrying cells. In order to trigger a tumor antigen-specific humoral immune response, therefore, various forms of MUC1 and CEA were utilized as immunogens by others (e.g. in recombinant poxvectors; Bronte et al., J. Immunol. 154:5282, 1995) in animal models and preliminary clinical trials.

Non-malignant normal body cells are tolerated by the immune system, the body reacts to a normal cell by means of an immune response if the cell synthesizes proteins foreign to the body, e.g. as the result of a viral infection. MHC molecules present foreign peptides which originate from the foreign proteins. Subsequently, the immune system registers that something undesirable and alien has happened to this cell. Antigen presenting cells (APC)s, including macrophages, dendritic cells, Langerhans cells, and B-cells are activated, a new specific immunity is generated and the cell is eliminated.

A fucose-containing glycoprotein fraction from *Ganoderma lucidum* may thus be used as an adjuvant to trigger or intensify a cellular and/or humoral, preferably systemic, immune response to pathogens or an anti-tumor antigen.

In a further aspect, the disclosure provides a method of augmenting the ability of antigen presenting cells (APC) to present tumor antigens to the immune system, the method comprising contacting antigen presenting cells with a composition comprising a fucose-containing glycoprotein fraction from *Ganoderma lucidum* prior to, or simultaneously with, or after, the loading of the antigen presenting cell with tumor antigen(s). In one implementation, the antigen presenting cells are contacted with the fucose-containing glycoprotein fraction and the tumor antigen ex vivo, and are then introduced into a subject that is carrying a tumor that bears the tumor antigen(s). APCs include dendritic cells and macrophages. The composition comprising the fucose-containing glycoprotein fraction may enable or enhance the charging ("transloading") of APCs with the tumor antigen or fragments. Proteins or protein fragments thus absorbed are processed by the cells and can then be presented to the immune effector cells in the MHC context and thus trigger or intensify an immune response (Braciale, T. J. and Braciale, V. L., 1991, Immunol. Today 12, 124-129; Kovacsovics Bankowski, M. and Rock, K. L., 1995, Science 267, 243-246; York, I. A. and Rock, K. L., 1996, Ann. Rev. Immunol. 14, 369-396).

The triggering of a cellular immune response can be confirmed by detecting antigen-specific CTLs, for example in Current Protocols in Immunology, Chapter 3, or in Blomberg, K. and Ulfstedt, A. C., 1993, J. Immunol. Methods 160:27-34. Another indication of the presence of a cellular immune response is provided when, in the absence of T-cells, there is no immune response in an experimental animal (which is achieved by treating the animal with antibodies which deplete the CD4- or CD8-cells) (Current Protocols in Immunology, Chapter 3). A cellular immune response can also be demonstrated by detecting a "delayed-type hypersensitivity" (DTH) reaction in immunized animals. For this purpose, peptides are injected into the sole of the paw in mice and the swelling at the injected site is measured (Grohmann, U. et al., 1995, *Eur. J. Immunol.*, 25, 2797-2802; Puccetti, P., et al., 1995, *Eur. J. Immunol.*, 24, 1446-1452).

The induction of a humoral immune response by foreign antigens to the organism or antigens expressed in low concentrations by the organism to be treated, can be determined by detecting specific antibodies in the serum. A suitable method of detecting the antibody level in the serum is enzyme-linked immunoassay (ELISA). The specific antibodies are detected, after binding to the peptide used for immunisation, by means of a staining reaction. An alternative method is Western blot. In this, specific serum antibodies bind to the peptide immobilised on a membrane. Bound antibodies are finally detected again with a staining reaction (reference for both methods: *Current Protocols in Immunology*, Editors: Coligan et al., 1991).

Pharmaceutical Compositions

According to another aspect, the fucose-containing glycoprotein fraction from *Ganoderma lucidum* can be included in a pharmaceutical composition together with additional active agents, carriers, vehicles, excipients or auxiliary agents identifiable by a person skilled in the art upon reading of the present disclosure.

The pharmaceutical compositions preferably comprise at least one pharmaceutically acceptable carrier. In such pharmaceutical compositions, the fucose-containing glycoprotein forms the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration.

Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

"Subject" as used herein refers to humans and non-human primates (e.g. guerilla, macaque, marmoset), livestock animals (e.g. sheep, cow, horse, donkey, pig), companion animals (e.g. dog, cat), laboratory test animals (e.g. mouse, rabbit, rat, guinea pig, hamster), captive wild animals (e.g. fox, deer) and any other organisms who can benefit from the agents of the present disclosure. There is no limitation on the type of animal that could benefit from the presently described agents. The most preferred subject of the present disclosure is a human. A subject regardless of whether it is a human or non-human organism may be referred to as a patient, individual, animal, host or recipient.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of the active compound (i.e., an effective dosage) may range from about 0.001 to 30 mg/kg body weight. The skilled artisan will appreciate that certain factors can influence the dosage and timing required to effectively treat a subject, including but not limited to the severity of the disease or disorder, previous treatments, the general health and/or age of the subject, and other diseases present.

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLES

The present disclosure is further described by the following non-limiting examples. Materials, methods and statistical analyses used in the following examples are described in Wang et al., *Bioorg. Med. Chem.*, 10 (2002) 1057-1062; Hsu et al., "Extract of Reishi Polysaccharides Induces Cytokine Expression via TLR4-Modulated Protein Kinase Signaling Pathways", *J. Immunol.* (2004) 173, 5989-5999; Chien C., Chen J., Chang W., Tien M. Tsao C. Chang Y. Chang H., Hsieh J., Wong C. and Chen S., *Bioorg. Med. Chem.*, 2004, 12, pp. 5603-5609; Chen H., Tsai Y., Lin S., Lin C., Khoo K., Lin C. and Wong C., Studies on the immuno-modulating and anti-tumor activities of *Ganoderma lucidum* (Reishi) polysaccharides, *Bioorg. Med. Chem.*, 2004 vol. 12, iss. 21, pages 5595-5601, and Lin et al., *J. Biol. Chem.*, 281 (34) 24111-24123, (2006), each of of which is herein incorporated by reference in its entirety. Examples 1-3 show variations in scale of preparation, analysis of Reishi crude extract and F3 extract, as well as further subfractionation techniques.

Example 1

Preparation and Analysis of Reishi Extracts F1, F2, F3, F4, and F5

Crude Reishi extract (prepared via alkaline extraction (0.1 N NaOH), neutralization and ethanol precipitation) was obtained from Pharmanex Co. (CA, USA). Preparation and characterization of a fucose-containing glycoprotein fraction from *Ganoderma lucidum* is described in Wang et al., *Bioorg. Med. Chem.* 10 (2002) 1057-1062. A larger scale preparative method is described in Lin et al., *J. Biol. Chem.*, 281 (34) 24111-24123, (2006). Briefly, twenty-eight mg of the crude extract were dissolved in 2 mL of Tris buffer (pH 7.0, 0.1 N) and centrifuged to remove the insoluble materials (7 mg). The supernatant was purified by gel filtration chromatography using a Sephacryl S-500 column (100×1.6 cm) with 0.1 N Tris buffer (pH 7.0) as the eluent. The flow rate was set at 0.5 mL/min, and the eluate (7.5 mL per tube) was collected. Tubes were pooled as follows to give five fractions: fraction 1: 100-130 mL; fraction 2: 130-155 mL; fraction 3: 155-205 mL; fraction 4: 205-220 mL; and fraction 5: 220-255 mL.

The main fraction having an optical density (O.D.) of about 1.8 at 625 nm was designated as Fraction 3. After chromatography, the crude extract and each of the isolated fraction were subjected to anthrone analysis (Somani B. L., Khanade J. and Sinha R. *Anal. Biochem.* 167 (1987), p. 327; Jermyn M. A. *Anal. Biochem.* 1975 (68), p. 332; Halhoul M. N. and Kleinberg I., *Anal. Biochem.* 1972 (50), p. 337) to detect sugar components. Fractions 1-5 were each dialyzed to remove excessive salt and lyophilized to give 1.0 mg, 6.2 mg, 5.3 mg, 2.1 mg, and less than 1 mg, respectively.

In a scaled-up preparative example, Reishi-F3 extract was prepared by a method analogous to example 1 above. A 2.1 gram sample of filtered, lyophilized Reishi crude extract returned 520 mg (25% yield) of Reishi F3 extract (Lin et al., 2006).

Sugar Composition Analysis: Anthrone Colorimetric Method

Each 1.5 mL of anthrone (9,10-dihydro-9-oxoanthracene) solution (0.2 g anthrone dissolved in 100 mL of concentrated sulfuric acid) in a series of test tubes immersed in an ice water bath was carefully overlayed with 1.5 mL of sample (20-40 µg/mL of -glucose or equivalent). After all additions had been made, the tubes were shaken rapidly and then replaced in an ice water bath. The tubes were heated for 5 min in a boiling water bath and then cooled; the optical densities were read within an hour at 625 µm against distilled water. Standards, reagent blanks and unknowns were run in triplicate because of likely contamination by other carbohydrate sources. Calculations were made on the basis that the optical densities are directly proportional to the carbohydrate concentration.

Sugar Composition Analysis—TMS Method

For monosaccharide analysis, the polysaccharide extracts/fractions were methanolyzed with 0.5 M methanolic-HCl (Supelco) at 80° C. for 16 h, re-N-acetylated with 500 µL of methanol, 10 µL of pyridine and 50 µL of acetic anhydride, and then treated with the SYLON HTP® trimethylsilylating reagent (Supelco) for 20 min at room temperature, dried and redissolved in hexane. GC-MS analysis of the trimethylsilylated derivatives was carried out using a Hewlett-Packard (HP) Gas Chromatograph 6890 connected to a HP 5973 Mass Selective Detector. Samples were dissolved in hexane prior to splitless injection into a HP-5MS fused silica capillary column (30 m×0.25 mm I.D., HP). The column head pressure was maintained at around 8.2 psi to give a constant flow rate of 1 mL/min using helium as carrier gas. Initial oven temperature was held at 60° C. for 1 min, increased to 140° C. at 25° C./min, to 250° C. at 5° C./min, and then increased to 300° C. at 10° C./min.

The carbohydrate composition of crude extract is reported in Table I, the carbohydrate composition of crude Reishi extract and of Fraction 3 is reported in Tables I and II, respectively, below.

TABLE I

| Carbohydrate compositions of crude Reishi extract | |
|---|---|
| Sugar components | Percentage (%) |
| D-Glucose | 58.0 |
| D-Mannose | 15.5 |
| L-Fucose | 9.7 |
| D-Galactose | 9.3 |
| D-Xylose | 5.4 |
| D-GlcNAc | 1.0 |
| L-Rhamnose | 0.5 |

TABLE II

Carbohydrate compositions of Fraction 3

| Sugar components | Percentage (%) |
|---|---|
| D-Glucose | 58.1 |
| D-Mannose | 15.1 |
| L-Fucose | 7.1 |
| D-Galactose | 13.5 |
| D-Xylose | 3.1 |
| D-GlcNAc | 1.2 |
| L-Rhamnose | 0.7 |

High pH anion-exchange chromatography with pulsed amperometric detection (HPAEC/PAD) analysis, confirmed that F3 includes a glycoprotein or polysaccharide comprising fucose residues.

Also $H_2SO_4$/phenol analysis showed that overall polysaccharides concentration in F3 (85%) is higher than crude extract (60%).

Amino Acid Composition Analysis

The analysis was carried out based on a well-established method (Spachman D. H., Moore S. and Stein W. H., *Anal. Chem.* 30 (1958), p. 1190; Lo, C.-H.; Chiou, S.-H. *J. Chromatogr.* 1990, 530, 129). A sample of crude Reishi extract (6 mg) was dissolved in 1 mL solution of 6 M HCl and TFA (4/1), and heated at 140° C. for 3 h. The mixture was concentrated to give a dry residue and dissolved in 100 µL citrate buffer. A small aliquot (4 µL) was withdrawn and subjected to composition analysis by amino acid analyzer (Jeol JLC-6AH).

The resulting amino acid composition of Reishi Crude extract is shown in Table III below.

TABLE III

Amino acid analysis of Reishi extract

| Amino acid | Relative abundance |
|---|---|
| Asp | 117 |
| Thr | 66 |
| Ser | 54 |
| Glu | 120 |
| Pro | 60 |
| Gly | 108 |
| Ala | 100 |
| Val | 61 |
| Met | 6 |
| Ile | 36 |
| Leu | 55 |
| Tyr | 16 |
| Phe | 28 |
| His | 12 |
| Lys | 21 |
| Arg | 22 |

Reishi crude extract contained approximately 15.6% protein by amino acid analysis. Further analysis of protein concentration in Reishi crude extract and in Reishi-F3 showed F3 to contain approximately 10% protein, and Reishi crude extract to contain approximately 20% protein by the Lowrey method with BSA as a standard.

Further analysis of F3 carbohydrate composition, including differences between carbohydrate composition of F3 and subfractions, as well as procedures to obtain F3 subfractions, can be found in Chen et al., *Bioorg. Med. Chem.* 12 (2004) 5595-5601 which is incorporated herein in its entirety.

Example 2

Preparation and Purification of Reishi Extracts
F3—Subfractionation to Produce F3G1 FRG2,
F3GH1, and F3GH2

Crude Reishi extract (prepared via alkaline extraction (0.1 N NaOH), neutralization and ethanol precipitation) was obtained from Pharmanex Co., (CA, USA). All the chemicals and reagents were from Sigma Co., (St. Louis, Mo., USA) unless indicated.

Crude Reishi extract (100 g) was dissolved in 3 L of double distilled water, stirred at 4° C. for 24 h, and centrifuged for 1 h to remove the insoluble. The resulting solution was concentrated at 35° C. to give a small volume and lyophilized to generate 70 g powder of dark-brown color, 2.5 g of which were dissolved in a small volume of Tris buffer (pH 7.0, 0.1 N), and purified by gel filtration chromatography using a Sephacryl S-500 column (95×2.6 cm) with 0.1 N Tris buffer (pH 7.0) as the eluent. The flow rate was set at 0.6 mL/min, and 7.5 mL per tube was collected. After the chromatography, each fraction was subjected to anthrone analysis or the phenol-sulfuric acid method as described in Example 1 above, to detect sugar components. Five fractions were collected (fractions 1-5), each dialyzed to remove excessive salt and lyophilized, to give 450 mg of each fraction and in particular of F3.

F3 was further subjected to a column of Diaion-WA30 anion exchanger (Cl⁻ form, 40×3.5 cm) eluted with 0.2 and 0.8 M NaCl at a flow rate of 0.5 mL/min, and two fractions were designated as F3G1 (11% yield based on F3) and F3G2 (10% yield based on F3), respectively. Another fraction (F3G3, 11% yield based on F3) was generated when the column was further eluted with 2 M NaOH.

The carbohydrate composition of the F3G1, F3G2 and F3G3 was determined by anthrone colorimetric method and TMS method. The results are shown in Table IV below.

TABLE IV

Carbohydrate compositions of F3, F3G1, F3G2, and F3G3

| | Percentage (%) | | | | | | |
|---|---|---|---|---|---|---|---|
| | L-Fuc | D-Xyl | D-Man | D-Gal | D-GlcNAc | D-Glc | Unknown |
| F3 | 7.1 | 3.1 | 15.1 | 13.5 | 1.20 | 58.1 | 1.90 |
| F3G1 | 8.0 | 5.7 | 10.2 | 12.6 | 0.25 | 63.2 | 0.05 |
| F3G2 | 6.2 | 4.5 | 18.3 | 5.3 | 0.78 | 64.9 | 0.02 |
| F3G3 | 8.4 | 7.2 | 14.5 | 2.9 | 1.18 | 65.7 | 0.12 |

The results show that both Fraction 3 and the subfractions F3G1, F3G2 and F3G3 comprise glucose and mannose as major components together with smaller amounts of other sugars, including fucose N-acetylglucosamine, xylose and rhamnose, The percentage of galactose is apparently less in F3G2 and F3G3 than in other fractions.

Gel-filtration chromatography of F3G2 was carried out on a TSK HW-75 column (130×2.6 cm) eluted with double distilled water at a flow rate of 0.5 mL/min. Two fractions were collected; F3G2H1 (19% yield based on F3G2) and F3G2H2 (69% yield based on F3G2).

Further indications concerning the composition of F3G1, F3G2, F3G3, F3G2H1 and F3G2H2 and procedures to obtain the subfractions can be found in Chen et al., 2004, herein incorporated in its entirety.

Example 3

Preparation of Reishi Extract Fraction 3

A crude *G. Lucidum* PS extract prepared via alkaline extraction with 0.1 N of NaOH, followed by neutralization and ethanol precipitation, was obtained from Pharmanex (CA). The crude *G. Lucidum* extract (100 g) was dissolved in 3 L of double-distilled $H_2O$ and stirred at 4° C. for 24 h. The solution was centrifuged (16,000 g) at 4° C. for 1 h, and the supernatant was concentrated at 35° C. The slurry product was then lyophilized to obtain 70 g of water-soluble dark brown *G. Lucidum* extract. The extract (2.5 g) was fractionated on Sephacryl S-500 column (95 2.6 cm) with 0.1 N of Tris buffer (pH 7.0) as the eluent. The flow rate was set at 0.6 ml/min, and fractions were collected with 7.5 ml per tube. Five fractions were collected, and each was dialyzed to remove excessive salts and lyophilized to give fractions 1-5; each fraction was characterized, as described in Example 1. The fucose-containing glycoprotein fraction (20~30% yield), i.e., Fraction 3 (F3), was isolated.

To avoid LPS contamination the crude *G. Lucidum* materials and PS extracts were prepared, from growth to harvest, as GMP grade from Pharmanex and the possible bacterial contamination was carefully monitored to meet the Food and Drug Administration standard. The reagents and utensils for preparation of F3 were either endotoxin-free grade or washed with PBS containing 50 μg/mL polymyxin B (PMB), then rinsed with PBS. F3 contained <1 ng of LPS/25 μg, as measured by LAL assay (Sigma-Aldrich). In addition, certain reagents were routinely checked by LAL for examination of LPS contamination.

An additional procedure was performed as described in Wang et al., *Biorg. Med. Chem.* 10 (2002), 1057-1062 herein incorporated by reference in its entirety. According to a modified version of the procedure described in Wang et al., 2002 comprises, direct centrifugation, isolated polysaccharide from water-soluble Reishi sample which showed additional components as well as F3.

Briefly; the water soluble polysaccharide from crude powder of Reishi 1 g was centrifuged (5000 r.p.m., 2800 g) at 4° C. for 1 h to separate polysaccharide by centrifugal filtration with MWCO: 100K, the polysaccharide fraction was collected and lyophilized to give F3 (F3>100K) 172 mg (17%). This portion of polysaccharide showed the familiar HPLC profile of F3. F3 produced in this fashion was further analyzed in biofunctional assays described in Wang et al., 2002. For example, F3 produced in this fashion showed cytokine release from mouse splenocytes by RT-PCR.

Example 4

Mouse and Human Cell Culture and Reagents

Mouse splenic B cells were purified using B220 microbeads (Miltenyi Biotec) from 6-8 week-old C57/B16 mice, prdm1$^{f/f}$ CD19Cre+ or prdm1$^{f/f}$ CD19Cre- as previously described (Shapiro-Shelef, M., Lin, K. I., McHeyzer-Williams, L. J., Liao, J., McHeyzer-Williams, M. G., and Calame, K. (2003) Immunity 19, 607-620, Shaffer, A. L., Shapiro-Shelef, M., Iwakoshi, N. N., Lee, A. H., Qian, S. B., Zhao, H., Yu, X., Yang, L., Tan, B. K., Rosenwald, A., Hurt, E. M., Petroulakis, E., Sonenberg, N., Yewdell, J. W., Calame, K., Glimcher, L. H., and Staudt, L. M. (2004) Immunity 21, 81-93). Purified splenic B cells (purity >95%) were cultured at RPMI 1640 medium (GIBCO® BRL) containing 10% heat inactivated fetal bovine serum (FBS) (GIBCO® BRL), penicillin/streptomycin (100 U/mL), 2 mM L-glutamine and 50 μM 2-ME at the density of $2\times10^6$ cells/mL. Cells were stimulated with LPS (2.5 μg/mL from Sigma) or Reishi F3 (20 μg/mL) for various time points.

Human peripheral blood mononuclear cells (PBMC) were isolated by HISTOPAQUE®-1077 (Sigma) according to manufacturer's suggestion. Human peripheral CD19$^+$ cells were further purified by CD19 microbeads (Miltenyi Biotec). Enriched human B cells (purity >90%) were maintained at RPMI 1640 medium (GIBCO® BRL) containing 10% heat inactivated fetal bovine serum (GIBCO® BRL), penicillin/streptomycin (100 U/mL), and 2 mM L-glutamine. CD19$^+$ cells, at the density of $2\times10^6$ cells/mL, were either treated with Reishi-F3 (20 μg/mL) or IL-4 (100 U/mL from PeproTech)+CD40L (1 μg/mL from PeproTech) at indicated time. Various inhibitors including SB203580, LY294002, SP600125, PD98059 and NF-kB inhibitors were purchased from Calbiochem. Anti-mouse TLR4 (clone HTA125), anti-human/mouse TLR2 (clone T2.5), anti-human TLR4/MD-2 (clone MTS510) and isotype control antibody, rat IgG2a, were all purchased from eBioscience. Isotype control antibodies, for example mouse IgG1 and mouse IgG2a, were from Sigma. 3T3 cells were maintained at DMEM (GIBCO® BRL) supplemented with 10% FBS and penicillin/streptomycin (100 U/mL).

Example 5

ELISA and Beadlyte Human-Cytokine Detection

For the enzyme-linked immunosorbent assays (ELISAs), cell supernatants were harvested by centrifugation of the culture medium once at 2,000 rpm. Supernatants were then serially diluted in PBS containing 1% bovine serum albumin into 96-well plates coated with anti-mouse IgM, anti-human IgM or anti-human IgG (Bethyl laboratories, Inc.) antibody and incubated for 1 h at 37° C. The following procedures and methods for detecting captured mouse IgM, human IgM or human IgG were essentially followed by the manufacturer's suggestion (Bethyl laboratories, Inc.) using TMB as the substrate. The plates were subsequently read on a plate reader (Molecular Devices) at 450 nm.

Beadlyte cytokine/chemokine multiplex assays (Upstate cell signaling solutions) were employed using the Luminex xMAP bead array for the detection of multiple cytokines from Reishi F3 treated human peripheral B cells. The manufacturer's protocol was used essentially as written and detection was performed on a Luminex® 100TM instrument.

Example 6

Flow Cytometry

B cells were harvested and washed in PBS once and then further resuspended in PBS plus 2% FBS at the density of $10^6$ cell/mL. A total of $10^5$ cells were used for each staining. Antibodies used in one study were PE-conjugated anti-mouse syndecan-1 (BD PharMingen), PE-conjugated mouse anti-human CD19 (BD PharMingen), PE-conjugated anti-human CD86 (eBioscience). Cells were then analyzed by FACScalibur (Becton Dickinson) and CellQuest software.

Example 7

The Effects of Reishi Extract F3 on Dendritic Cells: DC Maturation and Activation with Release of Cytokines A fucose-containing glycoprotein fraction from *Ganoderma lucidum*, Reishi-F3, has specific actions on dendritic cells under special circumstances. Dendritic cells (DCs) are antigen-presenting cells (APC) which induce primary immune response by capturing and transferring antigen to the cells of adaptive immune system, such as T cells and B cells. DCs are not only critical for the induction of primary immune response, but also important for the regulation of T cell-mediated immune response. Polysaccharides purified from Reishi water-soluble extract induced DCs maturation and activation with the release of sets of cytokines, under certain conditions. These cytokines may participate in the biological actions (e.g. anti-inflammation, anti-cancer, etc.) of Reishi. Reishi extract F3 was prepared essentially as described above.

Dendritic cells were derived from human peripheral blood mononuclear cells as shown in FIG. 1, which shows a scheme for preparation and induction of dendritic cells. Mononuclear cells were prepared from buffy coat by centrifugation against Ficoll-Paque plus (Amersham Bioscience) density gradient. $CD14^+$ mononuclear cells were purified using anti-CD14 microbeads and magnetic-activated cell sorting (MACS) system (Miltenyi Biotec). Purified $CD14^+$ cells (purity>90%) were cultured in RPMI1640 supplemented with 10% fetal calf serum, 1000 U/mL GM-CSF and 50 ng/mL IL-4. After 6 days induction, F3 fraction of Reishi was added for further 24 hours treatment.

Figure 2:
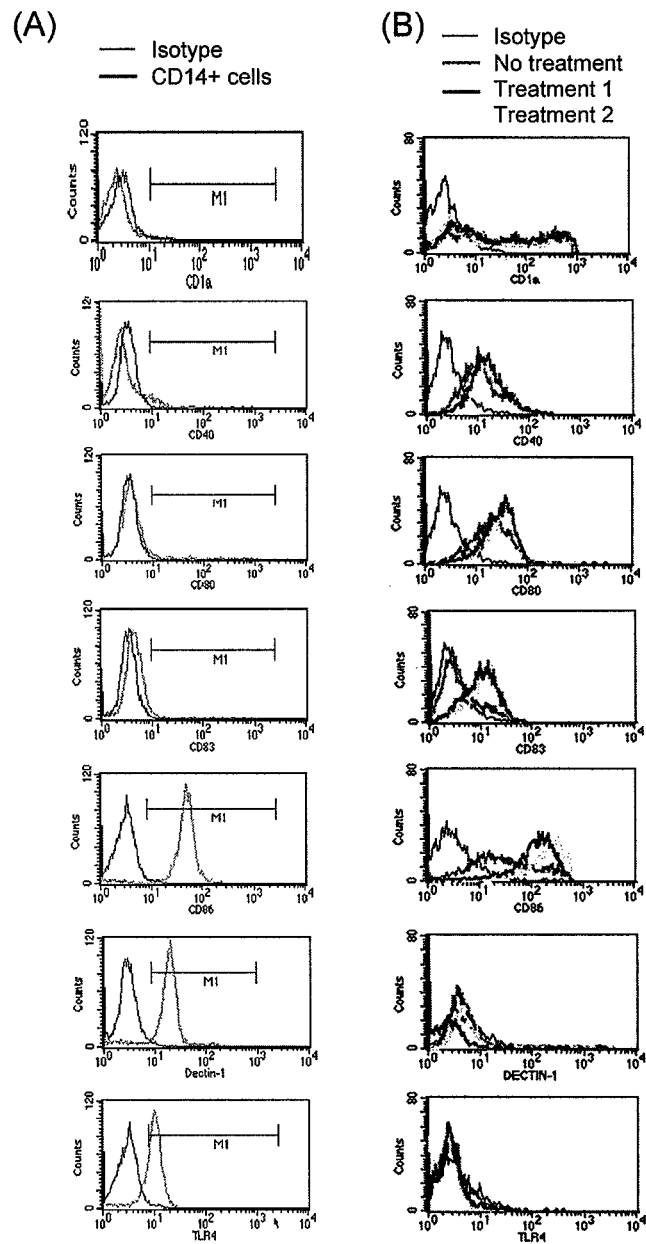
FIG. 2 shows histograms of some representative CD markers of dendritic cells stained on CD14+ monocytes and derived dendritic cells. 2(A) shows CD14$^+$ mononuclear cells (purity>90%), prepared at day 0 of induction (Black line: isotype control; grey line: CD14$^+$ MNC). 2(B) shows results when, after 6 days preculture induction, cells were treated with a fucose-containing glycoprotein fraction from *Ganoderma lucidum* (Reishi-F3). (Black line: isotype control; dark grey line: untreated control; medium grey and light grey lines: treated with a fucose-containing glycoprotein fraction from *Ganoderma lucidum*, two replicated experiments).

Immunophenotyping on cell surface markers was performed by FACS analysis and results are shown in FIG. 2. FIG. 2 shows histograms of some representative CD markers of dendritic cells stained on CD14+ monocytes and derived dendritic cells. FIG. 2(A) shows $CD14^+$ mononuclear cells (purity >90%), prepared at day 0 of induction (black line: isotype control; grey line: $CD14^+$ MNC). FIG. 2(B) shows results when, after 6 days preculture induction, cells were treated with Reishi polysaccharide extracts (black line: isotype control; dark grey line: untreated control; medium grey and light grey lines: treated with Reishi extract, two replicated experiments).

Untreated $CD14^+$ monocytes expressed CD14 and CD86, but no other dendritic cell markers were seen. After 6 days induction, cells lost $CD14^+$ marker and started to express dendritic cell markers including CD1a, CD40. After 24 hr Reishi F3 polysaccharides treatment, DCs increased the expression of CD80, CD83 and CD86 comparing with untreated control. On the other hand, if F3 was added on day 1, the proliferation of dendritic cells was inhibited.

Figure 3:
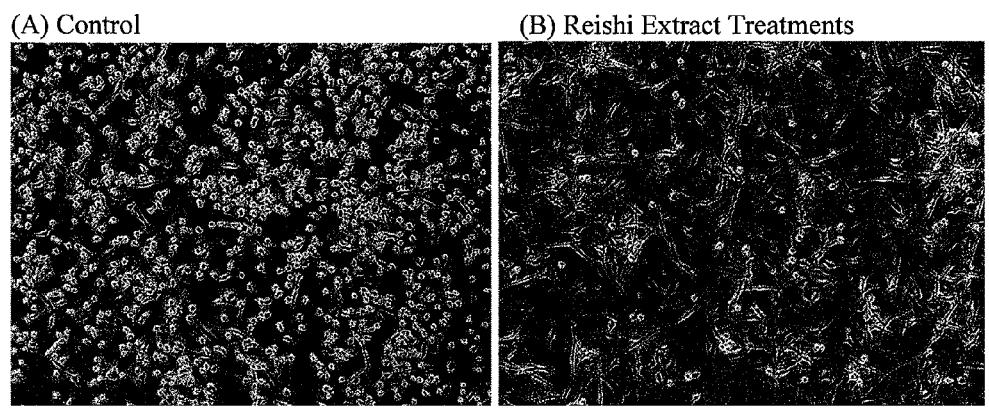
FIG. 3 shows morphological changes of dendritic cells being treated with a fucose-containing glycoprotein fraction from *Ganoderma lucidum* by conventional bright-field light microscopy. Cells loosely contacted to the surface in control group (A), but tightly adhered to culture wells with extended morphology (B).

Along with the crude Reishi extract or its derivative F3 treatment, the morphology of cells changed greatly as shown in microscopic photos in FIG. 3. FIG. 3 shows morphological changes of dendritic cells being treated with Reishi polysaccharide extracts by conventional bright-field light microscopy. Cells were loosely contacted to the surface in control group, FIG. 3(A), but tightly adhered to culture wells with extended morphology in the treated group, FIG. 3(B).

To reveal the cytokine secreting profile affected by Reishi-F3, DC culture media was collected in both treated and control group and evaluated in Example 8 below.

Example 8

The Effect of Reishi Extract on Cytokine Production

The cytokine secretion profile was determined in the Reishi extract treated and untreated dendritic cells described above in Example 7. The concentrations of cytokines and chemokines in the dendritic cell culture medium were measured using the Beadlyte® Human 22-Plex Multi-Cytokine Detection System (Upstate). The concentration of IL-1α, IL-1β, IL-3, IL-6, IL-7, IL-8, IL-10, IL-12p40, IL-12p70, IFN-K, TNF-α, Eotaxin, IP-10, MCP-1, MIP-1α, or RANTES were all found to be significantly increased following induction by Reishi extracts as shown in FIG. 4. FIG. 4 shows a table of cytokine secreting profiles of dendritic cells after treatment with a fucose-containing glycoprotein fraction from *Ganoderma lucidum* via commercially available Beadlyte cytokines kit. Results showed 16 of 22 cytokines tested were significantly induced by Reishi extracts. Changes in each cytokine level are presented in terms of fold increase of the measurement of treated group against that of control group.

A similar experiment in which human $CD19^+$ cells were used, showed that a fucose-containing glycoprotein fraction from *Ganoderma lucidum* significantly increased production of IL-6, IL-8, and MIP-1α in these cells.

Example 9

Effects of Reishi F3 on B Lymphocytes

Reishi F3 Induces Plasmacytic Differentiation in Mouse Primary Splenic B Cells

Reishi has previously been shown to stimulate murine splenic B lymphocytes proliferation (Shao, B. M., Dai, H., Xu, W., Lin, Z. B., and Gao, X. M. (2004) *Biochem Biophys Res Commun* 323, 133-141; Zhang, J., Tang, Q., Zimmerman-Kordmann, M., Reutter, W., and Fan, H. (2002) *Life Sci* 71, 623-638), but whether Reishi has the activity to promote the plasma cell formation has not been formally addressed.

Various previously published protocols (Hsu, H. Y., Hua, K. F., Lin, C. C., Lin, C. H., Hsu, J., and Wong, C. H. (2004) *J Immunol* 173, 5989-5999 Wang, Y. Y., Khoo, K. H., Chen, S. T., Lin, C. C., Wong, C. H., and Lin, C. H. (2002) *Bioorg Med Chem* 10, 1057-1062 Chen, H. S., Tsai, Y. F., Lin, S., Lin, C. C., Khoo, K. H., Lin, C. H., and Wong, C. H. (2004) *Bioorg Med Chem* 12, 5595-5601) were used in these experiments.

A fucose-containing glycoprotein fraction from *Ganoderma lucidum*, Reishi-F3, was used to investigate mode of action in B lymphocytes. It was first tested whether Reishi F3 could have an effect on inducing antibody secretion in purified murine B cell culture. As previously described (Zhang, J., Tang, Q., Zimmerman-Kordmann, M., Reutter, W., and Fan, H. (2002) *Life Sci* 71, 623-638), it was observed that Reishi-F3 treatment results in B cell activation as shown by the increased expression of the activation marker, CD86, on surfaces (data not shown) and the increased proliferation of murine splenic B cells after 3 days of treatment (about 3.5 fold).

Figure 5:
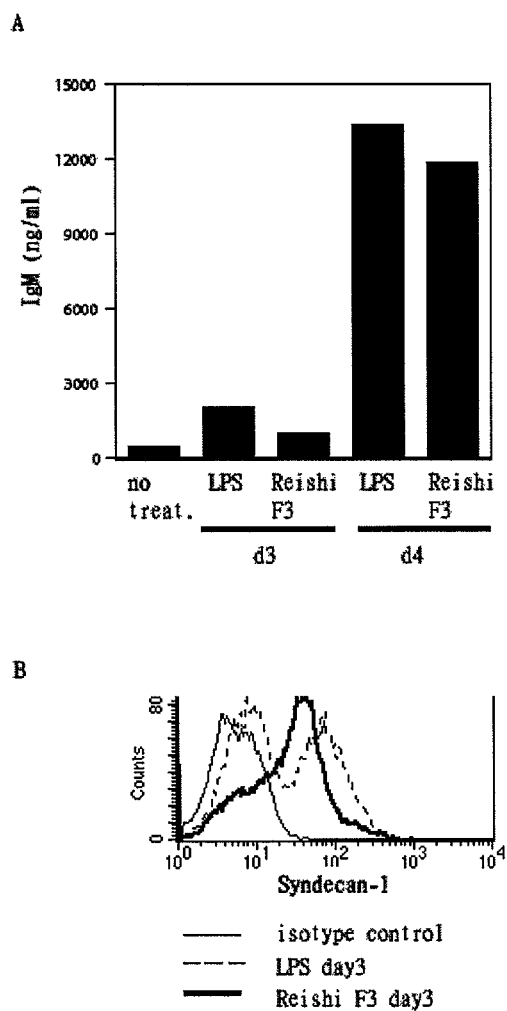
FIG. 5 shows a fucose-containing glycoprotein fraction from *Ganoderma lucidum* (Reishi-F3) induced plasmacytic differentiation in mouse primary splenic B cell culture. (A) Purified mouse splenic B cells were cultured with LPS (2.5 μg/mL) or a fucose-containing glycoprotein fraction from *Ganoderma lucidum* (Reishi-F3) (20 μg/mL). Cell supernatants were harvested at day 3 and day 4 for ELISA analysis to determine the amount of IgM. Reishi-F3 induced IgM secretion in mouse splenic B cells similar to LPS. (B) Primary splenic B cells were harvested at day 3 after treatment with LPS or Reishi-F3 and subjected to flow cytometry analysis to view the expression of surface CD138. Reishi-F3 (20 μg/mL) induced up-regulation of plasma cell surface marker (CD138).

Reishi-F3 induced plasmacytic differentiation in mouse primary splenic B cell culture. Purified mouse splenic B cells were cultured with lipopolysaccharide (t) (2.5 μg/mL) or Reishi F3 (20 μg/mL). Cell supernatants were harvested at day 3 and day 4 for ELISA analysis to determine the amount of IgM present. Significantly, as shown in FIG. 5A, compared to cells without Reishi-F3 treatment, a dramatic induction of IgM began to be detected by ELISA after treatment of splenic $B220^+$ B cells with Reishi-F3 for 3 days. A further increased IgM induction was observed at day 4 (FIG. 5A). It has been previously observed that treatment of primary murine splenic B cells cultured ex vivo with the polyclonal mitogen lipopolysaccharide (LPS) gives rise to a burst of proliferation followed by subsequent differentiation to immunoglobulin secreting plasma cells (Sieckmann, D. G., Asofsky, R., Mosier, D. E., Zitron, I. M., and Paul, W. E. (1978) *J. Exp. Med.* 147, 814-829; Chen-Bettecken, U., Wecker, E., and Schimpl, A. (1985) *Proc. Natl. Acad. Sci. USA* 82, 7384-

7388). Reishi-F3 induced IgM secretion in mouse splenic B cells comparable to LPS induced IgM secretion (FIG. 5A).

A robust induction of expression of plasma cell surface marker, syndecan-1 (CD138) was observed in splenic B cell culture stimulated with Reishi-F3 for three days by FACS cytometry. Specifically, as shown in FIG. 5B, primary splenic B cells were harvested at day 3 after treatment with LPS or Reishi F3 and subjected to flow cytometry analysis to view the expression of surface CD138. Reishi-F3 (20 µg/mL) induced up-regulation of plasma cell surface marker (CD138). The possibility of LPS contamination during the Reishi-F3 preparation was carefully eliminated as previously described (Hsu, H. Y., Hua, K. F., Lin, C. C., Lin, C. H., Hsu, J., and Wong, C. H. (2004) *J. Immunol.*, 173, 5989-5999). Sodium azide was used during the initial preparation procedures of *Ganoderma lucidum* (Reishi) to prevent the growth of bacteria. NMR analysis also revealed differential signature of components between LPS and Reishi-F3 (W-B Yang unpublished data). These results suggest that Reishi F3 may have a role in promoting plasmacytic differentiation.

Example 10

Effects of F3 on B Lymphocytes

The Effects of Reishi on Primary Human Peripheral B Cell Activation

Reishi-F3 was also evaluated for its effect on the activation and/or differentiation of human peripheral B cells isolated from healthy donors. Purified human $CD19^+$ cells from peripheral blood were treated with Reishi and the expression of B cell activation marker CD86 was analyzed by flow cytometry after various time points. Cells treated with anti-IgM, CD40 ligand (CD40L) and IL-4 were used here as the positive control for B cell activation.

Figure 6:
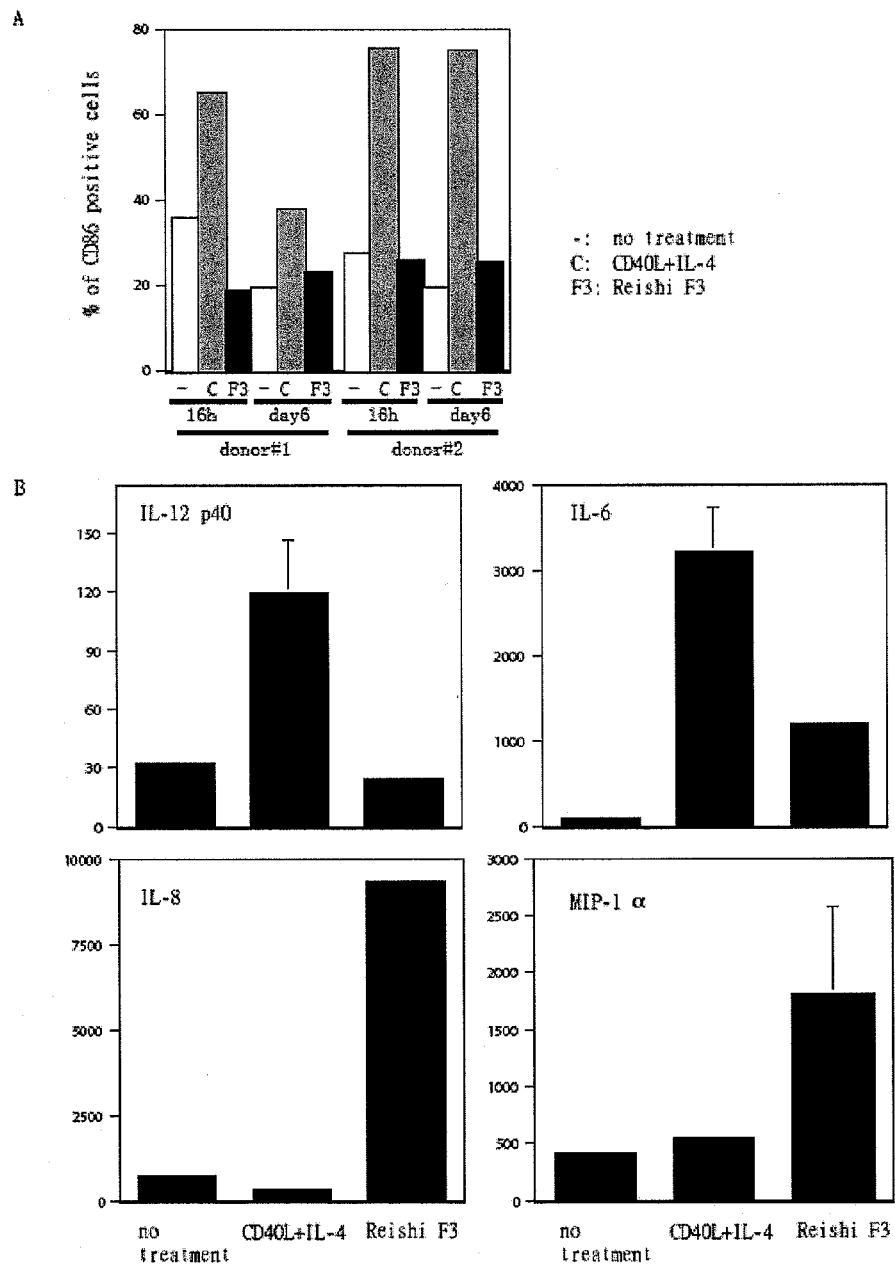
FIG. 6 shows Reishi-F3 treatment results in an increased expression of different cytokines or chemokines in human peripheral B cell culture. (A) Unlike cytokine treatment, Reishi-F3 treatment could not activate human peripheral B cells. Isolated human peripheral CD19$^+$ cells were treated with cytokine (C: CD40L (1 μg/mL) +IL-4 (100 U/mL)), Reishi-F3 (F3: 20 μg/mL) or left untreated (−). Cells were harvested at 16 hours or 6 days after the treatment for FACS analysis of CD86 expression on the surface. The percentage of positive cells in each culture was shown. The results represent one of the three cultures. (B) Reishi-F3 induced production of IL-6, IL-8 and MIP-1α. Purified human peripheral B cells were treated as described in (A) and cell supernatants were harvested at day 6 for detection of a panel of cytokines or chemokines. The results represent one of the three independent cultures; standard deviation was shown.

Results are shown in FIG. 6. Treatment with Reishi-F3 caused only slight increase of cell number at day 6 (about 10% increase), while the combination treatment of CD40L and IL-4 caused around 50% increase of cell number, compared to cells without treatment (data not shown). Although the significant induction of B cells activation marker, CD86, was observed in positive control groups, CD40L+IL-4 stimulated B cells (FIG. 6A), peripheral B cells showed no significant effect on the expression of CD86 at early (16 hours) or late (6 days) time points of Reishi-F3 treatment (FIG. 6A). Similar results were observed by the analysis of another activation marker CD69 (data not shown). Therefore, unlike the effect of Reishi F3 in activating mouse splenic B cells, Reishi-F3 could not activate human peripheral B lymphocytes.

The effect of Reishi-F3 on stimulation of the generation of various cytokines or chemokines from peripheral B lymphocytes was monitored by Beadlyte cytokine/chemokine multiplex assays luminex technology. An array of expression of cytokines and chemokines were tested using the cultured supernatant from human $CD19^+$ B cells treated with Reishi F3, CD40L+IL-4 or no treatment for 6 days. No induction was seen on a panel of cytokines or chemokines, like IL-1α, IL-1β, IL-3, IL-10, IL-12p70, IL-13, IL-15, IL-2, IL-3, IL-4, IL-5, IL-7, IP-10, MCP-1, RANTES, and TNFα, by Reishi F3 (data not shown).

However, a robust induction of IL-6, IL-8 and MIP-1α by Reishi-F3 treatment was observed (FIG. 6B). The induction of IL-8 appeared to be limited to Reishi-F3 treatment. Thus, Reishi-F3 can't induce the expression of B cell activation marker, CD86, but it seemed to sufficiently induce the secretion of some cytokines or chemokines; particularly IL-8 and MIP-1α.

Figure 7:
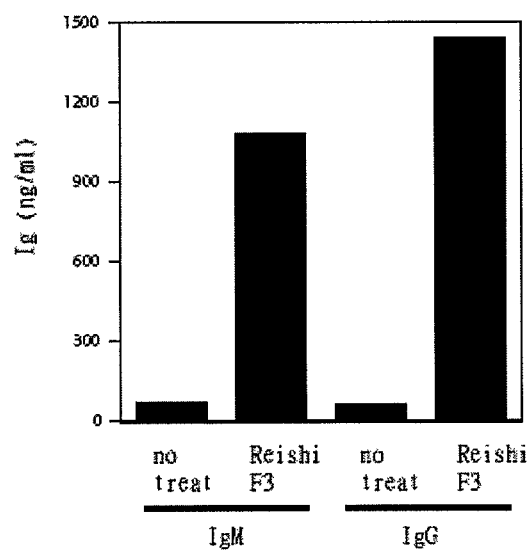
FIG. 7 shows Reishi-F3 caused a significant induction of IgM and IgG in human CD19$^+$ B cells by ELISA.

Although Reishi-F3 failed to activate human peripheral $CD19^+$ B cells (FIG. 6A), it caused a significant induction of IgM and IgG in human $CD19^+$ B cells (FIG. 7). FIG. 7 shows Reishi F3 caused a significant induction of IgM and IgG in human $CD19^+$ B cells by ELISA. Therefore, unlike its effect in both activating B cells and differentiating plasma cells in mouse splenic cells, Reishi-F3 could only induce the secretion of Ig in human peripheral B cells. Taken together, these results suggest Reishi functions on inducing Ig, cytokine and chemokine secretion in isolated human peripheral B cells.

Many modifications and variations are possible in the light of the above teachings. The foregoing is a description of the preferred embodiments of the disclosure and has been presented for the purpose of illustration and description. It is not intended to be exhaustive and so limit the disclosure to the precise form disclosed.

The disclosures of each and every publication and reference cited in the present description, which include any accompanying papers, which form part thereof, are hereby incorporated by reference in their entirety, in the present disclosure. The citation of each publication and reference is not to be taken as an admission that the disclosure of that publication and reference forms part of the body of prior art in any country.

REFERENCES

1) U.S. Provisional Application Ser. No. 60/727,047.
2) Shiao, M. S., K. R. Lee, L. J. Lin, and C. T. Wang. in *Food Phytochemicals for Cancer Prevention II. Teas, Spices, and Herbs*. C. T. Ho, T. Osawa, M. T. Huang, and R. T. Rosen, eds. American Chemical Society, Washington D.C., 1994, p. 342-354.
3) Sone, Y., R. Okuda, N. Wada, E. Kishida, and A. Misaki. in Agric. Biol. Chem. 1985 49:2641-2653.
4) Wang S.-Y., Hsu M.-L. and Hsu H., *Int. J. Cancer* 1997, 70, pp. 699-705.
5) Vetvicka V., Thornton B. P. and Ross G. D., *J. Clin. Invest.* 1996 98, pp. 50-61.
6) Van Strijp J. A. G., Russel D. G., Tuomanen E., Brown E. J. and Wright S. D., *J. Immunol.* 1993 151, pp. 3324-3336.
7) Muller A., Rice P. J., Ensley H. E., Coogan P. S., Kalbfleisch J. H., Kelley J. L., Love E. J., Portera C. A., Ha T., Browder I. W. and Williams D. L., *J. Immunol.*, 1996 156, pp. 3418-3425.
8) Lee, S. S., Y. H. Wei, C. F. Chen, S. Y. Wang, and K. Y. Chen. In J. Chin. Med. 1995 6:1-12.
9) Wong et al., WO 2006/44616, published Apr. 27, 2006.
10) Wang et al. (2002) *Biorganic & Medicinal Chemistry* 10: 1057-1062.
11) U.S. Pat. No. 6,471,860.
12) Norkin et al., Exp. Cell. Res. 266(2):229-38 (2001).
13) Handbook of Flow Cytometry Methods. J. Paul Robinson (Editor) Wiley (1993).
14) Guide To Flow Cytometry Methods W. McLean, Grogan James, M. Collins. Marcel Dekker, Inc, New York, (1990).
15) *Current Protocols in Molecular Biology*, John Wiley & Sons, N.Y. (2005), 11.1-11.3.
16) *Medical Microbiology*, Second Edition, (1990) J. C. Sherris (ed.), Elsevier Science Publishing Co., Inc., New York.
17) Feltkamp, M. C. et al., 1995, Eur. J. Immunol. 25 (9), 2638-2642.
18) Vitiello, A. et al., 1995, J. Clin. Inv. 95, 1, 341-349.

19) Widmann, C. et al., 1992, J. Immunol. Methods 155 (1), 95-99.
20) International Publication No. WO 93/05789.
21) Robbins, P. F. and Rosenberg, S. A., 1996, Journ. Exp. Med. 183, 1185-92.
22) Henderson, R. A., and Finn, O. J. 1996, Advances in Immunology 62, 217-256.
23) Bronte et al., J. Immunol. 154:5282, 1995.
24) Braciale, T. J. and Braciale, V. L., 1991, *Immunol. Today* 12, 124-129.
25) Kovacsovics Bankowski, M. and Rock, K. L., 1995, *Science* 267, 243-246.
26) York, I. A. and Rock, K. L., 1996, *Ann. Rev. Immunol.* 14, 369-396.
27) *Current Protocols in Immunology*, Chapter 3, Editors: Coligan et al., 1991.
28) Blomberg, K. and Ulfstedt, A. C., 1993, *J. Immunol. Methods* 160:27-34.
29) Grohmann, U. et al., 1995, *Eur. J. Immunol.* 25, 2797-2802.
30) Puccetti, P. et al., 1995, *Eur. J. Immunol.* 24, 1446-1452.
31) *Current Protocols in Immunology*. Editors: Coligan et al., 1991.
32) U.S. Pat. No. 4,522,811.
33) Wang et al., *Bioorg. Med. Chem.* 10 (2002) 1057-1062.
34) Lin et al., *J. Biol. Chem.*, 281 (34) 24111-24123, (2006).
35) Chen H., Tsai Y., Lin S., Lin C., Khoo K., Lin C. and Wong C., Studies on the immuno-modulating and anti-tumor activities of Ganoderma lucidum (Reishi) polysaccharides, *Bioorg. Med. Chem.*, 2004 vol. 12, iss. 21, pages 5595-5601.
36) Chien C., Chen J., Chang W., Tien M. Tsao C. Chang Y. Chang H., Hsieh J., Wong C. and Chen S., *Bioorg. Med. Chem.*, 2004, 12, pp. 5603-5609.
37) Hsu, H. Y., K. F., Lin, C. C., Lin, C. H., Hsu, J., and Wong, C. H., Extract of Reishi Polysaccharides Induces Cytokine Expression via TLR4-Modulated Protein Kinase Signaling Pathways, *J. Immunol.* (2004) 173: 5989-5999.
38) Somani B. L., Khanade J. and Sinha R. *Anal. Biochem.* 167 (1987), p. 327.
39) Jermyn M. A. *Anal. Biochem.* 1975 (68), p. 332.
40) Halhoul M. N. and Kleinberg I. *Anal. Biochem.* 1972 (50), p. 337.
41) Spachman D. H., Moore S. and Stein W. H. *Anal. Chem.* 30 (1958), p. 1190.
42) Lo, C.-H.; Chiou, S.-H. *J. Chromatogr.* 1990, 530, 129.
43) Shapiro-Shelef, M., Lin, K. I., McHeyzer-Williams, L. J., Liao, J., McHeyzer-Williams, M. G., and Calame, K. (2003) *Immunity* 19, 607-620
44) Shaffer, A. L., Shapiro-Shelef, M., Iwakoshi, N. N., Lee, A. H., Qian, S. B., Zhao, H., Yu, X., Yang, L., Tan, B. K., Rosenwald, A., Hurt, E. M., Petroulakis, E., Sonenberg, N., Yewdell, J. W., Calame, K., Glimcher, L. H., and Staudt, L. M. (2004) *Immunity* 21, 81-93.
45) Shao, B. M., Dai, H., Xu, W., Lin, Z. B., and Gao, X. M. (2004) *Biochem Biophys Res Commun* 323, 133-141.
46) Zhang, J., Tang, Q., Zimmerman-Kordmann, M., Reutter, W., and Fan, H. (2002) *Life Sci* 71, 623-638.
47) Sieckmann, D. G., Asofsky, R., Mosier, D. E., Zitron, I. M., and Paul, W. E. (1978) *J Exp Med* 147, 814-829.
48) Chen-Bettecken, U., Wecker, E., and Schimpl, A. (1985) *Proc Natl Acad Sci USA* 82, 7384-7388.

What is claimed is:

1. A method of increasing an immune response to an antigen in a subject identified as in need thereof, the method comprising:
   (a) contacting a cell population enriched for CD 14$^+$ mononuclear cells with the antigen and with a composition comprising a fucose-containing glycoprotein fraction from an alkaline extract of Ganoderma lucidum wherein the fucose-containing glycoprotein fraction includes fucose residues bound with α-1,2-fucosidic linkages;
   (b) cultivating ex vivo the CD14$^+$ mononuclear cells with the antigen and the fucose-containing glycoprotein fraction for a period of time sufficient to increase the differentiation of CD14+ cells into mature dendritic cells; and
   (c) subsequently administering the matured dendritic cells to the subject, wherein an immune response to the antigen by the subject is increased.

2. The method of claim 1, wherein the contacting is performed by administration in vivo of the antigen and the composition to the subject.

3. The method of claim 1, wherein the antigen is derived from a pathogen.

4. The method of claim 3, wherein the pathogen causes diphtheria, tetanus, pertussis, polio, Haemophilus Influenzae type b, hepatitis, pneumonia, meningitis, otitis media, influenza, avian flu, chicken pox, rubeola, or rubella.

5. The method of claim 1, wherein the antigen is expressed in a cancer cell.

6. The method of claim 1, wherein the alkaline extract is a sodium hydroxide (NaOH) extract.

7. The method of claim 1, wherein the fucose-containing glycoprotein fraction has an optical density (O.D.) of about 1.8 at 625 nm.

* * * * *